(12) United States Patent
Dong et al.

(10) Patent No.: US 7,569,571 B2
(45) Date of Patent: Aug. 4, 2009

(54) SUBSTITUTED PYRAZOLO [3,4-D]PYRIMIDINES AS CYTOKINE MODULATORS

(75) Inventors: Qing Dong, San Diego, CA (US); Jianqiang Wang, Acton, MA (US); Hengyuan Lang, San Diego, CA (US); Jiong Lan, Emeryville, CA (US)

(73) Assignee: Novartis AG, Basel (CH)

( * ) Notice: Subject to any disclaimer, the term of this patent is extended or adjusted under 35 U.S.C. 154(b) by 126 days.

(21) Appl. No.: 10/584,076

(22) PCT Filed: Dec. 23, 2004

(86) PCT No.: PCT/US2004/043682

§ 371 (c)(1), (2), (4) Date: Aug. 23, 2006

(87) PCT Pub. No.: WO2005/063766

PCT Pub. Date: Jul. 14, 2005

(65) Prior Publication Data

US 2007/0142405 A1  Jun. 21, 2007

Related U.S. Application Data

(60) Provisional application No. 60/575,113, filed on May 28, 2004, provisional application No. 60/532,529, filed on Dec. 23, 2003.

(51) Int. Cl.
- *C07D 487/04* (2006.01)
- *A61K 31/519* (2006.01)
- *A61P 35/04* (2006.01)
- *A61P 25/02* (2006.01)
- *A61P 25/06* (2006.01)
- *A61P 19/02* (2006.01)

(52) U.S. Cl. .................................... 514/262.1; 544/262

(58) Field of Classification Search ................. 544/262; 514/262.1, 151
See application file for complete search history.

(56) References Cited

U.S. PATENT DOCUMENTS 6,005,109 A * 12/1999 Faraci et al. ................. 546/119

FOREIGN PATENT DOCUMENTS

| WO | WO03/097062 A1 | 11/2003 |
| WO | WO03/099820 A1 | 12/2003 |

OTHER PUBLICATIONS

STN search downloaded Feb. 16, 2008.*

* cited by examiner

*Primary Examiner*—Brenda L Coleman
*Assistant Examiner*—Susanna Moore
(74) *Attorney, Agent, or Firm*—Mark W. Milstead

(57) ABSTRACT

Provided are bicyclic heterocycle-based p38 kinase, including p38α and p38β kinase, inhibitors. Pharmaceutical compositions containing the compounds are also provided. Methods of use of the compounds and compositions are also provided, including methods of treatment, prevention, or amelioration of one or more symptoms of p38 kinase mediated diseases and disorders, including, but not limited to, inflammatory diseases and disorders.

5 Claims, No Drawings

SUBSTITUTED PYRAZOLO [3,4-D]PYRIMIDINES AS CYTOKINE MODULATORS

RELATED APPLICATIONS

Priority is claimed herein to U.S. Provisional Patent Application Nos. 60/532,529, filed Dec. 23, 2003, and 60/575,113, filed May 28, 2004. Where national laws allow, the disclosures of the above-referenced provisional applications are incorporated herein in their entirety.

FIELD

Provided herein are bicyclic heterocyclic compounds which have cytokine inhibitory activity. Also provided are the uses of bicyclic heterocyclic compounds for treating conditions associated with p38α and β kinases and for treating p38 kinase-associated conditions.

BACKGROUND

A large number of cytokines participate in the inflammatory response, including IL-1, IL6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others (Henry et al., *Drugs Fut.*, 24:1345-1354 (1999); Salituro et al., *Curr. Med. Chem.*, 6:807-823 (1999)). Evidence in human patients indicates that protein antagonists of cytokines are effective in treating chronic inflammatory diseases, such as, for example, monoclonal antibody to TNF-α (Remicade) (Rankin et al., *Br. J. Rheumatol.*, 34:334-342 (1995)), and soluble TNF-α receptor-Fc fusion protein (Etanercept) (Moreland et al., 25 *Ann. Intern. Med.*, 130:478-486 (1999)).

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinases. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38α, p38β, p38γ, and p38δ. The α and β isoforms are expressed in inflammatory cells and are key modulators of TNF-α production. Inhibiting the p38α and β enzymes in cells results in reduced levels of TNF-α expression. Also, administering inhibitors of p38α and β in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

Pyrrolotriazine compounds useful as tyrosine kinase inhibitors are disclosed in U.S. patent application Ser. No. 09/573,829 filed May 18, 2000, assigned to Bristol-Myers Squibb. In addition, pyrrolotriazine kinase inhibitors are disclosed in WO 02/40486, assigned to Bristol-Myers Squibb. Recent applications: WO 03/032970, WO 03/033482, WO03/032971, WO 03/032986, WO 03/032980, WO 03/032987, WO 03/033483, WO 03/033457 and WO 03/032972 are incorporated into this application. A series of aminoaryl substituted 5- and 6-membered ring heterocycles useful as inhibitors of IMPH are disclosed in WO 00/25780. U.S. Pat. Nos. 6,005,109 and 6,103,900 disclose pyrazoles and pyrazolopyrimidines having CRF antagonistic activity. WO 03/090912 and WO 03/091229 disclose certain pyrrolotriazines useful as kinase inhibitors. Each of the patent applications, patents, and publications referred to herein is incorporated herein by reference.

SUMMARY

Compounds for use in compositions and methods for modulating the activity of cytokines are provided. In one embodiment, the compounds are used in compositions and methods for modulating p38 kinase, including, but not limited to p38α and p38β kinase activity. In certain embodiments, the compounds are bicyclic heterocyclic compounds that are substituted with a cycloalkylamide moiety. In certain embodiments, the compounds provided herein are substituted purines, pyrrolotriazines, pyrrazolopyrimidines, imidazolopyrimidines, and related compounds.

In one embodiment, provided herein are compounds of formula I:

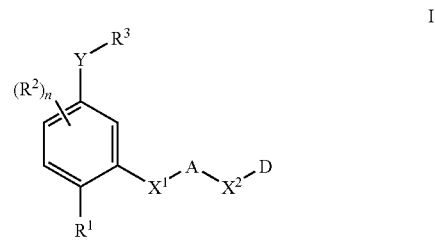

or pharmaceutically acceptable derivatives thereof, wherein:

$R^1$ is hydrogen, halo, alkyl, cycloalkyl, alkynyl, haloalkyl, alkoxy, haloalkoxy, pseudohalo, —$NR^4R^5$ or —$OR^4$;

$R^2$ at each occurrence is independently selected from alkyl, substituted alkyl, lower cycloalkyl, halo, trifluoromethyl, trifluoromethoxy, —$OR^4$, —CN, —$NR^4R^5$; —S(=O)alkyl, —S(=O)aryl, —$NHSO_2$-arylene-$R^4$, —$NHSO_2$alkyl, —$CO_2R^4$, —$CONH_2$, —$SO_3H$, —S(O)alkyl, —S(O)aryl, —$SO_2NHR^4$, and —NHC(=O)$NHR^4$;

n is 0, 1 or 2;

$R^3$ is selected from hydrogen, alkyl, —$OR^4$, substituted alkyl, cycloalkyl, —$CR^4$cycloalkyl, heteroaryl, substituted heteroaryl, heterocycle and substituted heterocycle;

Y is a single bond, —C(=O)NH—, —NH(C=O)—, —NH(C=O)NH—, —$SO_2NH$—, —$NHSO_2$— or —C(=O)—;

$X^1$ is a single bond, alkylene, —O—, —S—, —S(O)—, —SO$_2$—, —C(O)—, —CO(O)— or —C(O)NH—;

A is a bicyclic heterocyclic ring system with at least one heteroatom in each ring, where the heteroatoms are each independently selected from N, O and S, and is optionally substituted with up to two $R^{13}$;

$X^2$ is a single bond, alkylene, —O—, —S—, —NH—, —N(C$_{1-4}$alkyl)-, —NH—C$_{1-4}$alkylene-, —N(C$_{1-4}$alkyl)-C$_{1-4}$alkylene-, —S(O)—, —SO$_2$—, —C(O)—, —CO(O)— or —C(O)NH—;

D is a monocyclic or bicyclic aromatic or non-aromatic ring system optionally containing up to four heteroatoms selected from N, O, and S, and wherein a CH$_2$ adjacent to any of the said N, O or S heteroatoms is optionally substituted with oxo (=O), or D is C$_{1-6}$alkyl, and wherein D is optionally substituted by one to four (CR$^9$R$^{10}$)$_w$E groups;

w is an integer from 0-4;

$R^{10}$ is selected from H, C$_1$-C$_4$ alkylhydroxy, C$_1$-C$_4$alkylaryl and C$_1$-C$_4$alkylheteroaryl, wherein said aryl or heteroaryl group is unsubstituted or substituted with 1-3 groups independently selected from halo, NO$_2$, C$_1$-C$_4$alkyl, C$_3$-C$_{10}$cycloalkyl, C$_2$-C$_6$alkenyl, C$_2$-C$_6$alkynyl, haloalkyl, haloalkoxy, OH, C$_1$-C$_4$alkoxy, C$_1$-C$_4$alkylcarbonyl, CN, NH$_2$, NR$^6$R$^7$, SR$^6$, S(O)R$^6$, SO$_2$R$^6$, SO$_3$R$^6$, SO$_2$NR$^6$, CO$_2$H, CO$_2$R$^6$, and CONR$^6$R$^7$;

E is selected from H, halogen, NO$_2$, C$_1$-C$_4$alkyl, C$_3$-C$_{10}$cycloalkyl, C$_2$-C$_6$alkenyl, C$_2$-C$_6$ alkynyl, haloalkyl, haloalkoxy, OH, OR$^6$, CN, CHO, CO$_2$R$^6$, CONR$^6$R$^7$, OCOR$_6$, OC(=O)OR$^6$, OC(=O)NR$^6$R$^7$, OCH$_2$CO$_2$R$^6$, C(=O)R$^6$, NH$_2$, NHR$_6$, NR$^6$R$^7$, NR$^7$C(=O)R$^6$, NR$^7$C(=O)OR$^6$, NR$^7$C(=O)C(=O)OR$^6$, NR$^7$C(=O)C(=O)NR$^6$R$^7$, NR$^7$C(=O)C(=O)(C$_1$-C$_6$alkyl), NR$^7$C(=NCN)OR$^6$, NR$^7$C(=O)NR$^6$R$^7$, NR$^7$C(=NCN)NR$^6$R$^7$, NR$^7$C(=NR$^6$)NR$^7$R$^8$, NR$^6$SO$_2$NR$^6$R$^7$, NR$^7$SO$_2$R$^6$, SR$^6$, S(=O)R$^6$, SO$_2$R$^6$, SO$_3$R$^7$, SO$_2$NR$^6$R$^7$, NHOH, NHOR$^6$, NR$^6$NR$^7$NR$^8$, N(COR$^6$)OH, N(CO$_2$R$^6$)OH, CONR$^7$(CR$^9$R$^{10}$)$_r$R$^6$, CO(CR$^9$R$^{10}$)$_p$O(CHR$^9$)$_q$CO$_2$R$^6$, CO(CR$^9$CR$^{10}$)$_r$R$^6$, CO(CR$^9$R$^{10}$)$_p$, O(CR$^9$R$^{10}$)$_p$O(CHR$^9$)$_q$CO$^2$R$_6$, CO(CR$^9$CR$^{10}$)$_r$OR$^6$, CO(CR$^9$R$^{10}$)$_p$O(CR$^9$R$^{10}$)$_q$R$^6$, CO(CR$^6$CR$^{10}$)$_r$NR$^6$R$^7$, OC(O)O(CR$^9$R$^{10}$)$_m$NR$^6$R$^7$, O(CO)$_n$(CR$^9$R$^{10}$)R$^6$, O(CR$^9$R$^{10}$)$_m$NR$^6$R$^7$, NR$^7$C(O)(CR$^9$R$^{10}$)$_p$OR$^6$, NR$^7$C(=NC)(CR$^9$R$^{10}$)$_r$R$^6$, NR$^7$CO(CR$^9$R$^{10}$)$_r$NR$^6$R$^7$, NR$^7$(CR$^9$R$^{10}$)$_m$OR$^6$, NR$^7$(CR$^9$R$^{10}$)$_r$CO$_2$R$^6$, NR$^7$(CR$^9$R$^{10}$)$_m$NR$^6$R$^7$, NR$^7$, NR$^3$(CR$^9$R$^{10}$)$_n$SO$_2$(CR$^9$R$^{10}$)$_r$CO$_2$R$^6$, NR$^7$(CR$^9$R$^{10}$)$_m$NR$^6$R$^7$, NR$^7$(CR$^9$R$^{10}$)$_n$SO$_2$(CR$^9$R$^{10}$)$_q$R$^6$, CONR$^7$(CR$^9$R$_{10}$)$_n$SO$_2$(CR$^9$R$^{10}$)$_q$R$^6$, SO$_2$NR$^7$(CR$^9$R$^{10}$)$_q$R$^6$, SO$_2$NR$^6$(CR$^9$R$^{10}$)$_m$OR$^6$, C$_2$-C$_6$alkenyl, C$_3$-C$_{10}$cycloalkyl, C$_3$-C$_{10}$cycloalkylmethyl, aryl, heterocyclic optionally substituted with one or two alkyl groups, heteroaryl optionally substituted with one or two alkyl groups and alkylaryl, wherein said aryl groups are unsubstituted or substituted with 1 or 2 substituents each independently selected from R$^{12}$, or two E groups, which substitute adjacent atoms on D, together form alkylenedioxy, thioalkyleneoxy or alkylenedithioxy;

m is an integer having a value from 2-6;
p is an integer having a value from 1-3;
q is an integer having a value from 0-3;
r is an integer having a value from 0-6;

$R^{12}$ at each occurrence is independently selected from halo, NO$_2$, C$_1$-C$_4$alkyl, C$_3$-C$_{10}$cycloalkyl, C$_2$-C$_6$alkenyl, C$_2$-C$_6$alkynyl, haloalkyl, haloalkoxy, OH, oxo, C$_1$-C$_4$alkoxy, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$CN, O(CR$^9$R$^{10}$)$_r$C(=O)NR$^6$R$^7$, C$_1$-C$_4$alkylcarbonyl, CN, NH$_2$, NHR$^6$, NR$^6$R$^7$, NR$^7$(CR$^9$R$^{10}$)$_r$CO$_2$R$^6$, NR$^7$OR$^6$, NR$^7$(CR$^9$R$^{10}$)$_m$OR$^6$, NR$^7$CH((CR$^9$R$^{10}$)$_p$OR$^6$)$_2$, NR$^7$C((CR$^9$R$^{10}$)$_p$ OR$^6$)$_3$, NR$^7$C(=O)R$^6$, NR$^7$(CR$^9$R$^{10}$)$_m$NR$^6$R$^7$, NR$^7$(CR$^9$R$^{10}$)$_q$R$^6$, SR$^7$, S(O)R$^7$, SO$_2$R$^7$, SO$_2$NR$^6$, SO$_3$R$^7$, CO$_2$H, CO$_2$R$^6$, and CONR$^6$R$^7$;

$R^4$ is hydrogen, lower alkyl and lower cycloalkyl;
$R^5$ is hydrogen, lower alkyl and lower cycloalkyl;
$R^6$, $R^7$ and $R^8$ are independently selected as follows:

i) $R^6$, $R^7$ and $R^8$ are independently selected from H, C$_1$-C$_6$alkyl, C$_3$-C$_{10}$cycloalkyl, C$_2$-C$_6$alkenyl, C$_2$-C$_6$alkynyl, C$_1$-C$_6$alkylcarbonyl, C$_3$-C$_7$cycloalkyl (C$_0$-C$_5$alkyl)carbonyl, C$_1$-C$_6$alkoxycarbonyl, aryl(C$_0$-C$_5$alkyl)carbonyl, aryl(C$_1$-C$_5$alkoxy)carbonyl, heterocyclic(C$_0$-C$_5$alkyl)carbonyl, heterocyclic(C$_1$-C$_5$alkoxy)carbonyl, C$_1$-C$_6$alkylsulfonyl, arylsulfonyl, heteroarylsulfonyl, C$_0$-C$_4$alkylaryl, C$_0$-C$_4$alkylheterocyclic, wherein said cycloalkyl, aryl, or heterocyclic groups are unsubstituted or substituted with 1 or 2 substituents each independently selected from the group consisting of C$_1$-C$_4$alkyl, hydroxyl, C$_1$-C$_4$alkoxy, F, Cl, Br, haloalkyl, NO$_2$ and CN; or, ii) $R^6$ and $R^7$, or $R^6$ and $R^8$, or $R^7$ and $R^{8,}$ when both substituents are on the same nitrogen atom (as in (—NR$^6$R$^7$) or (—NR$^7$R$^8$)), can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo(3,2,2)nonan-3yl, and 1-tetrazolyl, the said heterocycle being optionally substituted with 1-3 groups each independently selected from oxo, C$_0$-C$_4$alkylOH, C$_0$-C$_4$alkylOC$_1$-C$_4$alkyl, C$_0$-C$_4$alkylCONH$_2$, C$_0$-C$_4$alkylCO$_2$C$_0$-C$_4$alkyl, C$_1$-C$_4$alkyl, C$_1$-C$_4$alkoxy, C$_3$-C$_7$cycloalkyl, C$_0$-C$_6$alkylcarbonyl, C$_3$-C$_7$cycloalkylcarbonyl, C$_1$-C$_6$alkoxycarbonyl, C$_3$-C$_7$cycloalkoxycarbonyl, —NHCOalkyl, aryl, heteroaryl, arylalkoxycarbonyl, heteroarylalkoxycarbonyl, C$_1$-C$_6$alkylsulfonyl, arylsulfonyl and heteroarylsulfonyl;

$R^9$ is hydrogen or C$_1$-C$_4$alkyl; and $R^{13}$ is hydrogen, alkyl, haloalkyl, aminocarbonyl, hydroxy, hydroxycarbonyl, alkoxycarbonyl, cycloalkylalkylaminocarbonyl, substituted alkyl, aryl, substituted aryl, heteroaryl, heterocyclyl, alkylthio, alkylaminocarbonyl or lower cycloalkyl; where the substituents on alkyl group are selected from one to four substituents selected from halo, hydroxy, alkoxy, oxo (=O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocycles, such as indolyl, imidazolyl, furyl, thienyl, thiazolyl, pyrrolidyl, pyridyl, pyrimidyl and the like and the substituents on aryl group are selected from one to four substituents selected from alkyl, substituted alkyl, haloalkyl, halo, trifluoromethoxy, trifluoromethyl, hydroxy, hydroxyalkyl, aminoalkyl, alkoxy, alkanoyl, alkanoyloxy, amino, arylamino, aralkylamino, dialkylamino, alkanoylamino, thiol, alkylthio, ureido, nitro, cyano, cyanoalkyl, heterocyclyl, carboxy, carboxyalkyl, carbamyl, alkoxycarbonyl, aminocarbonyl, alkylthiono, arylthiono, arylsulfonylamine, sulfonic acid, alkysulfonyl, sulfonamido, aryloxy and $CONR^aR^b$, where $R^a$ and $R^b$ are selected from hydrogen, alkyl, alkenyl, alkynyl, cycloalkyl, alkoxycarbonylaminoalkyl and alkylamino; or $R^a$ and $R^b$ together with the nitrogen on which they are substituted, form a 3-6 membered heterocyclic or heteroaryl ring. The substituent may be further substituted by hydroxy, alkyl, alkoxy, aryl, substituted aryl, substituted alkyl or aralkyl.

In one embodiment, the groups A, Y, $R^1$, $R^2$, $R^3$, $X^1$, $X^2$ and D are selected such that the resulting compound has effect on cytokine activity.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by cytokine activity, in one embodiment, p38 kinase activity, or in which cytokine activity, in one embodiment, p38 kinase activity is implicated, are also provided. The effective amounts and concentrations are effective for ameliorating any of the symptoms of any of the diseases or disorders.

Methods for treatment, prevention, or amelioration of one or more symptoms of diseases or disorders mediated by or in which cytokine activity, in one embodiment, p38 kinase activity, is implicated, are provided. Such methods include methods of treatment, prevention and amelioration of one or more symptoms of inflammatory diseases, autoimnmune diseases, destructive bone disorders, proliferative disorders, angiogenic disorders, infectious diseases, neurodegenerative diseases, and viral diseases, using one or more of the compounds provided herein, or pharmaceutically acceptable derivatives thereof.

Methods of modulating the activity of cytokines, in one embodiment, the activity of p38 kinases, using the compounds and compositions provided herein are also provided.

Methods of reducing the expression of inducible pro-inflammatory proteins, including, but not limited to prostaglandin endoperoxide synthase-2 (PGHS-2), also referred to as cyclooxygenase-2 (COX-2), in a subject in need thereof by administration of one or more compounds or compositions provided herein are also provided.

In practicing the methods, effective amounts of the compounds or compositions containing therapeutically effective concentrations of the compounds, which are formulated for systemic delivery, including parenteral, oral, or intravenous delivery, or for local or topical application, for the treatment of cytokine, in one embodiment, p38 kinase, mediated diseases or disorders, or diseases or disorders in which cytokine activity, in one embodiment, p38 kinase activity, is implicated, including, but not limited to, inflammatory diseases, autoimmune diseases, destructive bone disorders, proliferative disorders, angiogenic disorders, infectious diseases, neurodegenerative diseases, and viral diseases, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity cytokines, in one embodiment, p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated, within the packaging material, and a label that indicates that the compound or composition, or pharmaceutically acceptable derivative thereof, is used for modulating the activity of cytokine, in one embodiment, the activity of p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated, are provided.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, p38α refers to the enzyme disclosed in Han J, Richter B, Li Z, Kravchenko V, Ulevitch R J. Molecular cloning of human p38 MAP kinase. Biochim Biophys Acta. 1995; 1265(2-3):224-7. As used herein, p38β refers to the enzyme disclosed in Jiang Y, Chen C, Li Z, Guo W, Gegner J A, Lin S, Han J. Characterization of the structure and function of a new mitogen-activated protein kinase (p38beta). J Biol Chem. Jul. 26, 1996;271(30):17920-6. As used herein, p38γ refers to the enzyme disclosed in Li, Z.; Jiang, Y.; Ulevitch, R. J.; Han, J.: The primary structure of p38-gamma: a new member of p38 group of MAP kinases. *Biochem. Biophys. Res. Commun.* 228: 334-340, 1996. As used herein, p38δ refers to the enzyme disclosed in *Molecular Cloning and Characterization of a Novel p38 Mitogen-activated Protein Kinase,* Xuhong Sunny Wang, Katrina Diener, Carl L. Manthey, Shen-wu Wang, Bradley Rosenzweig, Jeffrey Bray, John Delaney, Craig N. Cole, Po-Ying Chan-Hui, Nathan Mantlo, Henri S. Lichenstein, Mark Zukowski and Zhengbin Yao.

The term "p38-associated condition", as used herein means any disease or condition in which p38 is known to play a role. This includes, conditions which are known to be caused by IL-1, TNF, IL-6 or IL-8 overproduction. Such conditions include, but are not limited to, inflamnmatory diseases, autoimmune diseases, destructive bone disorders, proliferative disorders, infectious diseases, viral disease, and neurodegenerative diseases.

As used herein inhibition of p-38α/βkinase means either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a p38 kinase mediated diseases or disorders, or diseases or disorders in which p38 kinase activity, including p38α activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of p38 kinase activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$^2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S($=$O) and S($=$O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S($=$O)—

(CRR)$_m$—, and —(CRR)$_n$—S(=O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH— CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur orsubstituted or unsubstituted nitrogen atoms, where the nitrogen substituent is alkyl. Alk(en)(yn)ylene groups include, but are not limited to, —C=C—(CH$_2$)$_n$— C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylid-ene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO2NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens. As another example, "C$_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944). Ceratin of the abbreviations used herein are listed below:

Ph=phenyl
Bz=benzyl
t-Bu=tertiary butyl
Me=methyl
Et=ethyl
Pr=propyl
Iso-P or iPr=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM or $CH_2Cl_2$=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl)-N,N,N',N'-tetramethyluronim hexafluorophosphate
KOH=potassium hydroxide
$K_2CO_3$=potassium carbonate
$POCL_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2SO_4$=sodium sulfate
$Na_2S_2O_3$=sodium thiosulfate
Pd=palladium
Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt=room temperature
$t_r$=HPLC retention time (minutes)
sat or sat'd=saturated B. Compounds In one embodiment, the compounds provided herein for use in the compositions and methods provided herein have formula I, where the variables are as described below. All combinations of such embodiments are within the scope of the instant disclosure.

In one embodiment, $R^1$ is hydrogen, lower alkyl, lower cycloalkyl, alkenyl or alkynyl. In another embodiment, $R^1$ is methyl, halo, hydroxyl, lower alkyl, lower cycloalkyl, lower alkynyl, trifluoromethyl, methoxy, trifluoromethoxy, cyano, $-NH_2$ or $-NR^4R^5$. In another embodiment, $R^1$ is methyl, halo, hydroxyl, lower alkyl, lower cycloalkyl, lower alkynyl, trifluoromethyl, methoxy, trifluoromethoxy, cyano, $-NH_2$, $-NR^4R^5$ or $-OR^4$. In another embodiment, $R^1$ is methyl, hydroxyl, lower alkyl, lower cycloalkyl, lower alkynyl, trifluoromethyl, methoxy, trifluoromethoxy, cyano, $-NH_2$, $-NR^4R^5$ or $-OR^4$. In one embodiment, $R^1$ is hydrogen or lower alkyl. In another embodiment, $R^1$ is hydrogen or methyl. In another embodiment, $R^1$ is methyl.

In another embodiment, $R^2$ is alkyl or cycloalkyl. In one embodiment, $R^2$ is hydrogen or alkyl. In one embodiment, $R^2$ is hydrogen or lower alkyl. In one embodiment, $R^2$ is hydrogen.

In another embodiment, $R^3$ is selected from hydrogen, alkyl, substituted alkyl, cycloalkyl, heterocyclyl and heteroaryl. In another embodiment, $R^3$ is selected from alkyl, $-OR^4$, substituted alkyl, cycloalkyl, $-CR^4$cycloalkyl, heteroaryl, substituted heteroaryl, heterocycle and substituted heterocycle. In one embodiment, $R^3$ is cycloalkyl, cycloalkylalkyl, alkoxyalkyl or heteroaryl. In one embodiment, $R^3$ is methyl, isopropyl, ethyl, cyclopropyl, cyclopropylmethyl, methoxymethyl, oxazolyl or thiazolyl. In another embodiment, $R^3$ is cyclopropyl.

In another embodiment, Y is $-C(=O)NH-$, $-NH(C=O)-$, $-NH(C=O)NH-$, $-SO_2NH-$, $-NHSO_2-$ or $-C(=O)-$. In another embodiment, Y is a single bond, $-C(=O)NH-$ or $-SO_2NH-$. In another embodiment, Y is $-C(=O)NH-$.

In another embodiment, $X^1$ is a single bond or alkylene. In another embodiment, $X^1$ is a single bond or $-CH_2-$. In another embodiment, $X^1$ is a single bond.

In another embodiment, A is a bicyclic heterocyclic ring system, where each ring contains at least one N atom, and is optionally substituted with up to two $R^{13}$. In another embodiment, A is a bicyclic heteroaryl ring system, where each ring contains at least one N atom, and is optionally substituted with up to two $R^{13}$. In another embodiment, A is a bicyclic heteroaryl ring system, where each ring contains two N atoms, and is optionally substituted with up to two $R^{13}$. In another embodiment, A is a imidazolopyrimidine, pyrrazolopyrimidine, imidazolopyrimidinone or pyrazolopyrimidinone group. In another embodiment, A is a imidazolopyrimidine or a pyrrazolopyrimidine group.

In another embodiment, $X^2$ is a single bond, alkylene or $-NH-$. In another embodiment, $X^2$ is a single bond, $-CH_2-$ or $-NH-$. In another embodiment, $X^2$ is a single bond.

In another embodiment, D is heterocyclyl, cycloalkyl, heteroaryl or aryl, and is optionally substituted by one to four, in one embodiment one or two, $(CR^9R^{10})_wE$ groups. In another embodiment, D is cyclohexyl, cyclopenyl, pyridyl, pyrimidinyl or phenyl, and is optionally substituted by one to four, in one embodiment one or two, $(CR^9R^{10})_wE$ groups. In another embodiment, D is phenyl and is optionally substituted by one to four, in one embodiment one or two, $(CR^9R^{10})_wE$ groups.

In another embodiment, A is optionally substituted with one $R^{13}$ group. In another embodiment, $R^{13}$ is alkyl, OH or $NH_2$. In another embodiment, $R^{13}$ is methyl, OH or $NH_2$.

In another embodiment, $(CR^9R^{10})_wE$ is alkyl, alkoxy, halo, $-CH2$-heterocyclyl, $-CONH$-cycloalkyl, alkylsulfonyl, alkylthio, alkylsulfonylamino, haloalkyl, aminocarbonyl, pseudohalo or heterocyclyl, or two $(CR^9R^{10})_wE$ groups, which substitute adjacent atoms on D, together form alkylenedioxy,. In another embodiment, $(CR^9R^{10})_wE$ is methoxy, methyl, 1,2,4-triazolyl, methylsulfonyl, ethoxy, 4-methyl-1-piperazinylmethyl, fluoro, chloro, cyclohexylaminocarbonyl, methanesulfonylamino, methylthio, 4-morpholinyl, trifluoromethyl, aminocarbonyl, iodo, cyano or cyclopropylaminocarbonyl, or two $(CR^9R^{10})_wE$ groups, which substitute adjacent atoms on D, together form methylenedioxy or ethylenedioxy.

In another embodiment, $R^1$ is halo, alkyl, cycloalkyl, alkynyl, haloalkyl, alkoxy, haloalkoxy, pseudohalo, $-NR^4R^5$ or $-OR^4$; and Y is $-C(=O)NH-$, $-NH(C=O)-$, $-NH(C=O)NH-$, $-SO_2NH-$, $-NHSO_2-$ or $-C(=O)-$.

In another embodiment, the compounds for use in the compositions and methods provided herein have formulae II:

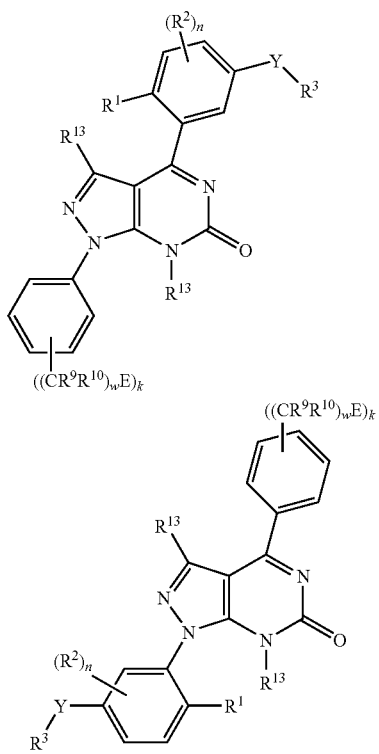

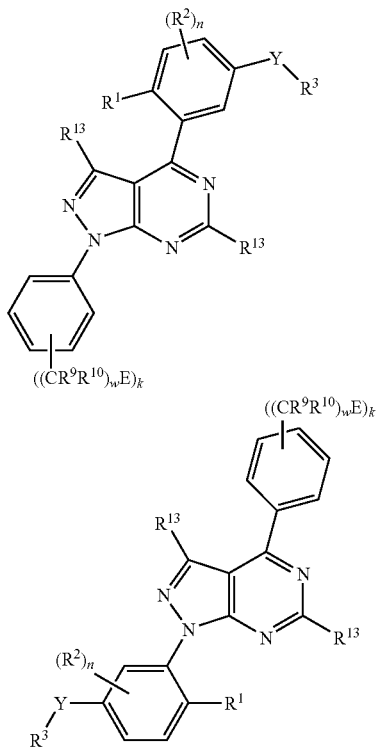

where k is an integer from 0 to 4; and the other variables are as defined above.

In another embodiment, the compounds for use in the compositions and methods provided herein have formula III:

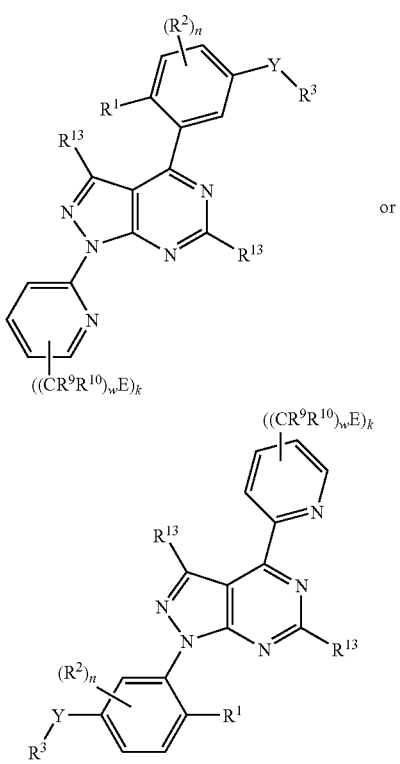

where the variables are as defined above.

In another embodiment, the compounds for use in the compositions and methods provided herein have formula IV:

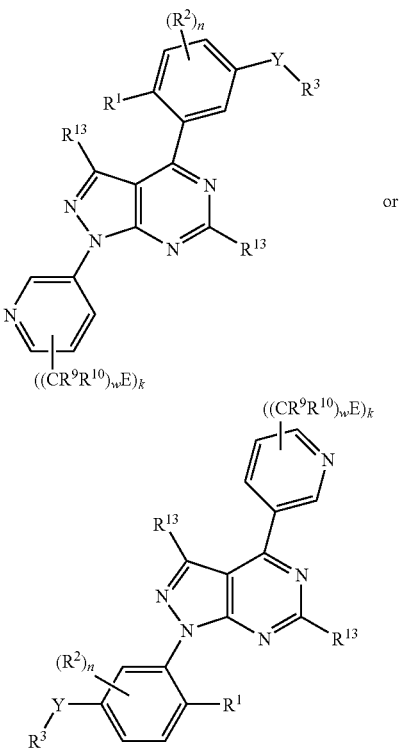

where the substituents are selected as above.

In another embodiment, the compounds for use in the compositions and methods provided herein have formula V:

where the substituents are selected as above.

In another embodiment, the compounds for use in the compositions and methods provided herein have formula VI:

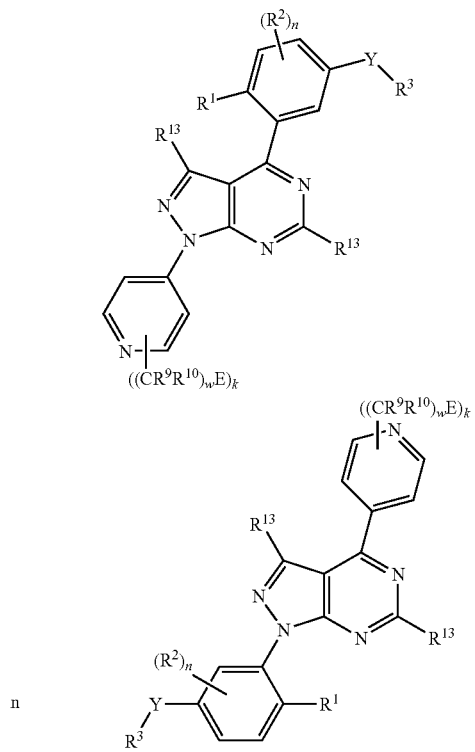

or

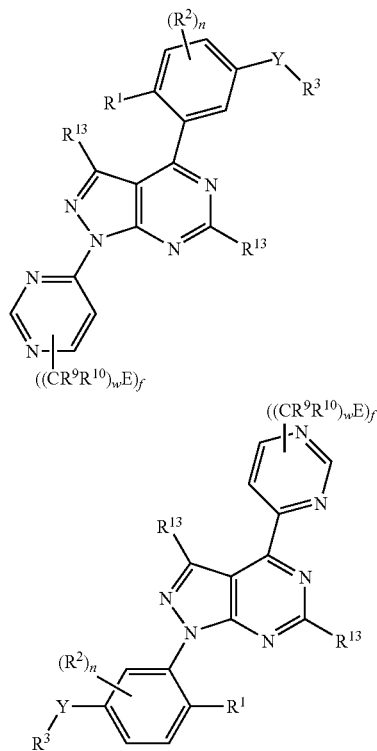

where the substituents are selected as above.

In another embodiment, the compounds for use in the compositions and methods provided herein have formula VII:

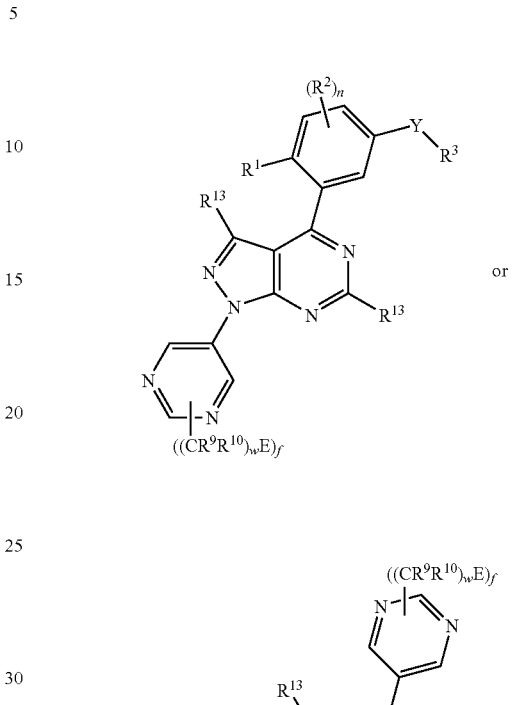

or

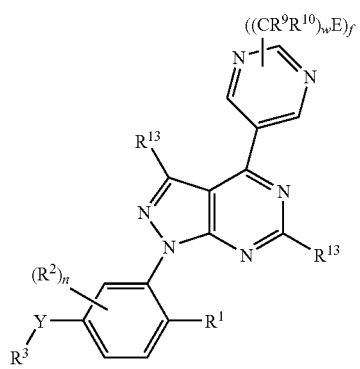

where f is an integer from 0 to 3; and the remaining variables are selected as above.

In another embodiment, the compounds for use in the compositions and methods provided herein have formula VIII:

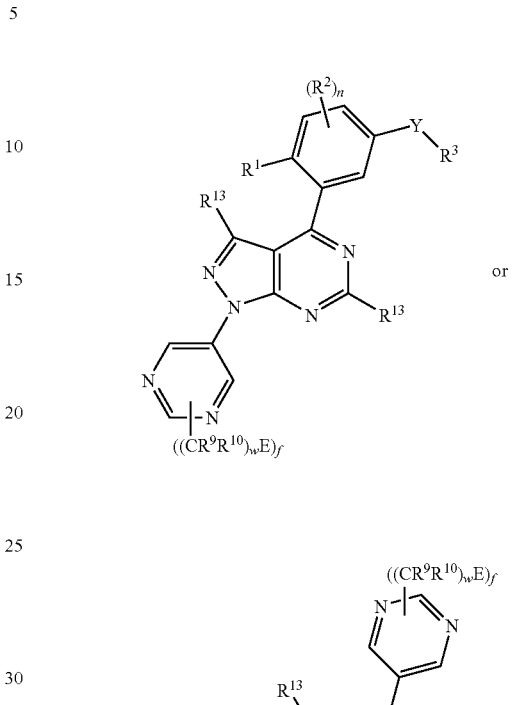

or

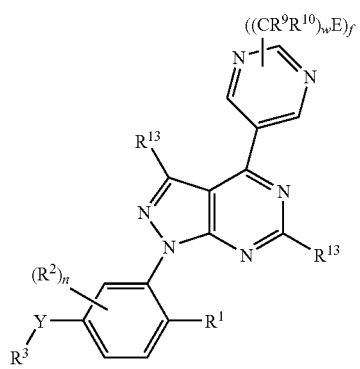

where the variables are as defined above.

In another embodiment, the compounds for use in the compositions and methods provided herein have formulae IX:

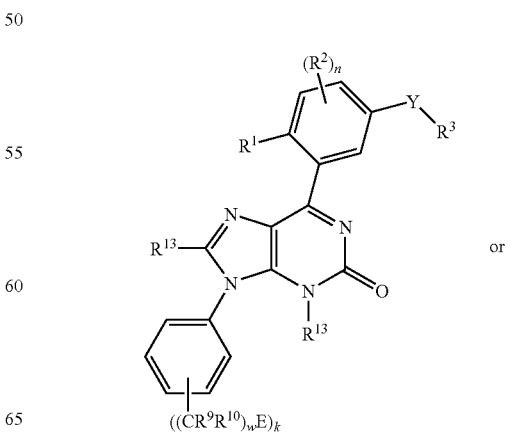

or

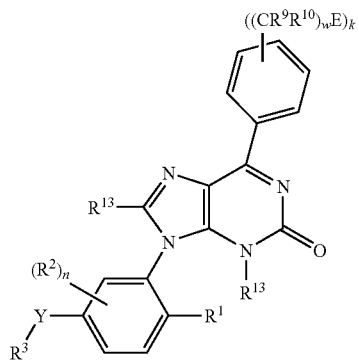

where k is an integer from 0 to 4; and the other variables are as defined above.

In another embodiment, the compounds for use in the compositions and methods provided herein have formula X:

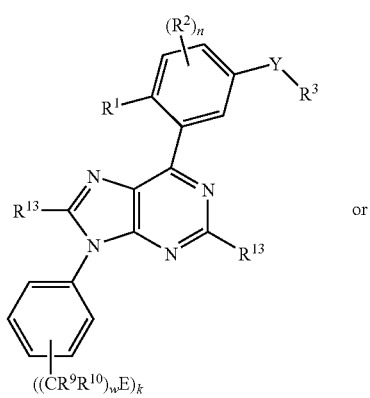

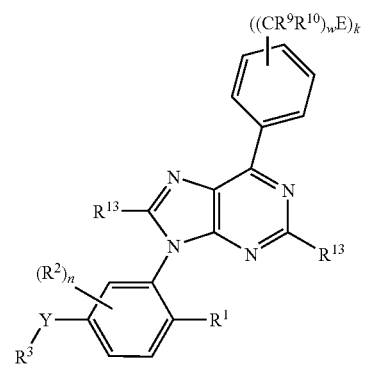

where the variables are as defined above.

In another embodiment, the compounds for use in the compositions and methods provided herein have formula XI:

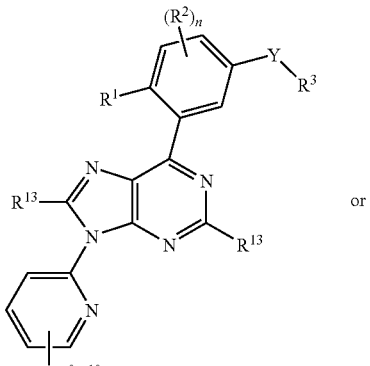

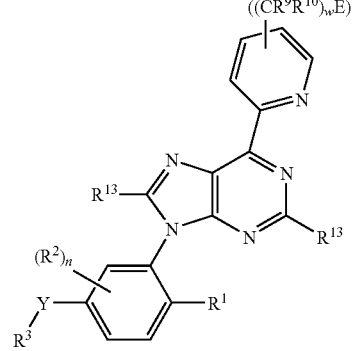

where the substituents are selected as above.

In another embodiment, the compounds for use in the compositions and methods provided herein have formula XII:

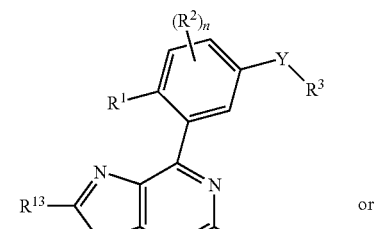

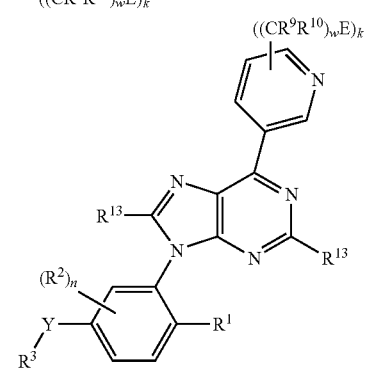

where the substituents are selected as above.

In another embodiment, the compounds for use in the compositions and methods provided herein have formula XIII:

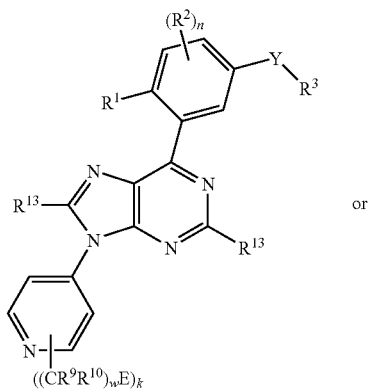

or

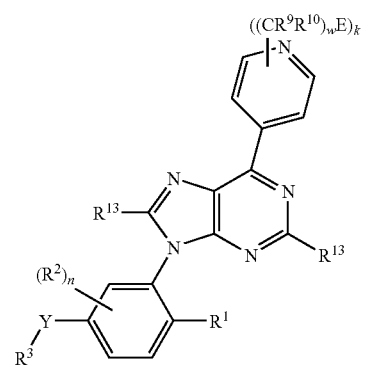

where the substituents are selected as above.

In another embodiment, the compounds for use in the compositions and methods provided herein have formula XIV:

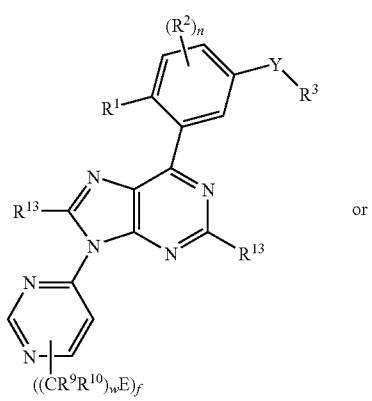

or

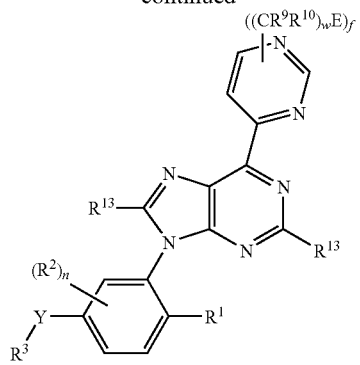

where f is an integer from 0 to 3; and the remaining variables are selected as above.

In another embodiment, the compounds for use in the compositions and methods provided herein have formula XV:

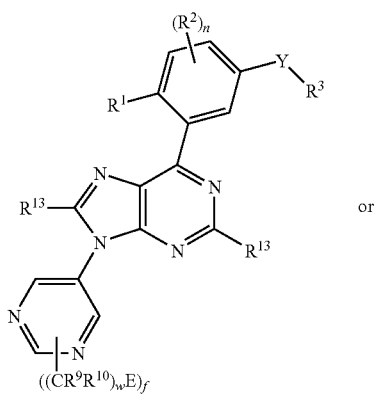

or

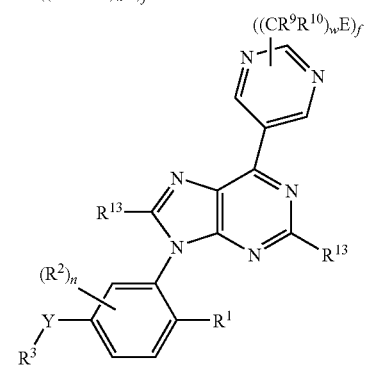

where the variables are as defined above.

In another embodiment, the compounds are selecte from those shown in the EXAMPLES.

C. Preparation of the Compounds

Compounds provided herein may be generally be prepared according to the following schemes and the knowledge of one skilled in the art. In addition to the documents incorporated by reference we disclose the following. Examples of methods useful for the production of compounds provided herein are illustrated in schemes 1-5.

Appropriately substituted 1H-pyrazolo[3,4-d]pyrimidines of type (I), which are useful herein, can be made by several means, for example as shown in scheme 1, the acid-catalyzed cyclization of (5-amino-1H-pyrazol-4-yl)-ketones with formamide.

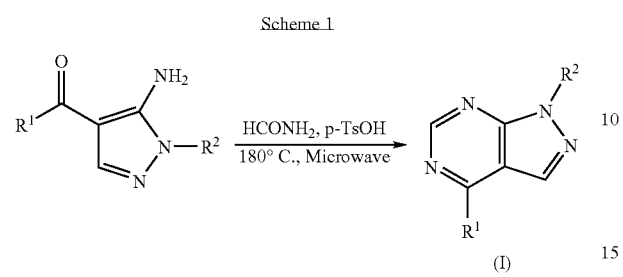

Appropriately substituted 9H-purines of type (II), which are useful herein, can be made by several means, for example as shown in scheme 2, the acid-catalyzed cyclization of (5-amino-1H-imidazol-4-yl)-ketones with formamide.

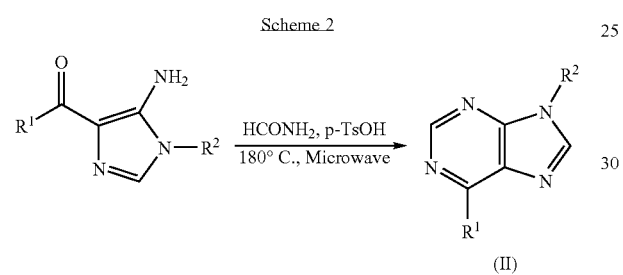

Alternatively, 9H-purines of type (III) bearing a 6-aryl substituent can be prepared by several means, for example as shown in Scheme 3. The microwave-mediated reaction between 4,6-dichlorpyrimin-5-ylamine and an appropriately substituted amine in a solvent such as NMP in the presence of a base such as DIEA, at a temperature preferably between 60° C. and 250° C., yields the monosubstituted pyrimidine. This intermediate is treated with triethyl orthoformate and a catalytic acid such as acetic acid to provide the 6-chloro-purine intermediate. The 6-chloro-purine thus obtained can be treated in the microwave with an appropriately substituted organometallic reagent such as a tributyl stannane or an appropriately substituted boronic acid under palladium(0) catalysis in a solvent such as DMF or dioxane at a temperature preferably between 60° C. and 150° C. to provide the desired substituted purine.

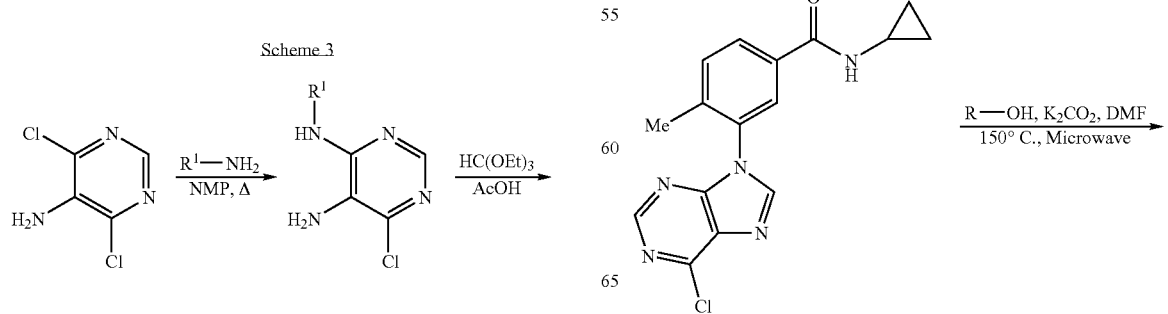

-continued

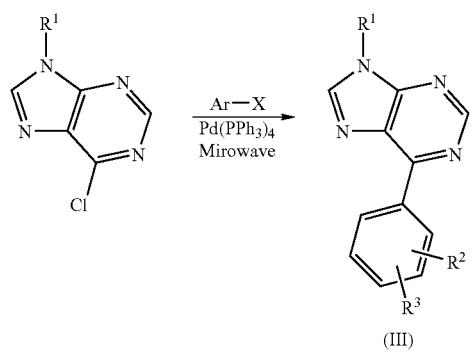

Alternatively, 9H-purines of type (III) bearing a 6-aryl substituent can be prepared by several means, for example as shown in Scheme 4

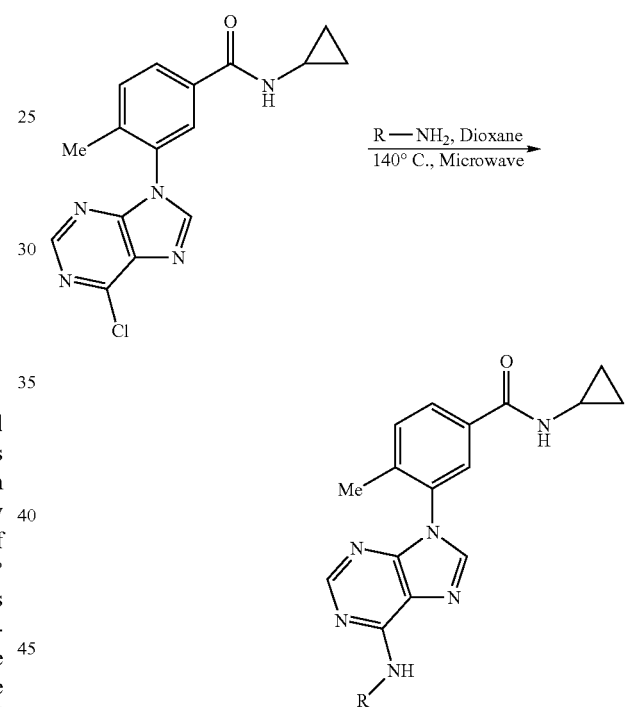

Alternatively, 9H-purines of type (III) bearing a 6-aryl substituent can be prepared by several means, for example as shown in Scheme 5

-continued

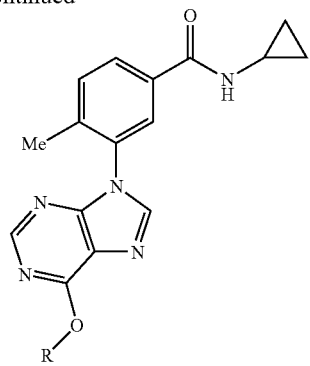

Appropriately substituted 5-amino4-acyl-pyrazoles of type (IV), which are useful herein as intermediates for the preparation of 1H-pyrazolo[3,4-d]pyrimidines of type (I), can be made by several means, for example as shown in scheme 4. An appropriately substituted 3-oxo-propionitrile is treated with diphenylformamidine in a solvent such as toluene or xylene at a temperature preferably between 60° C. and 150° C. The intermediate thus obtained can be treated with an appropriately substituted hydrazine in a solvent such as ethanol at a temperature preferably between 50° C. and 100° C. to yield the 4-acyl-5-aminopyrazole. A base such as triethylamine or diisopropylethylamine can be added to the reaction mixture to neutralize in situ any hydrazine obtained as a hydrochloride or trifluoroacetate salt. The 3-oxo-propionitriles useful herein can be purchased commercially or prepared by several means, for example from esters by the reaction with the lithium salt of acetonitrile as disclosed in WO 99/57101 and shown in Scheme 4a.

Scheme 4

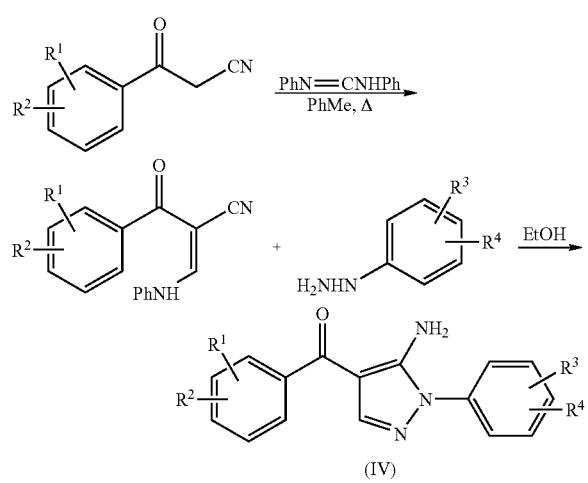

Scheme 4a

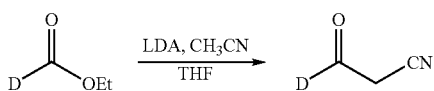

Appropriately substituted 5-amino4-acyl-imidazoles of type (V), useful as intermediates for the preparation of 9H-purines of type (II), can be made by several means, for example as shown in scheme 5. Appropriately substituted amines can be treated with triethyl orthoformate in the microwave at a temperature between preferably between 60° C. and 150° C. The intermediate thus obtained can be treated with aminomalonitrile tosylate and a catalyst such as p-toluenesulfonic acid in a solvent such as acetic acid to provide the 5-amino-1H-imidazole-4-carbonitrile. Reaction of the carbonitrile with an organometallic reagent such as a Grignard reagent in a solvent such as THF followed by acid hydrolysis yields the 4-acyl-5-aminoimidazole.

Scheme 5

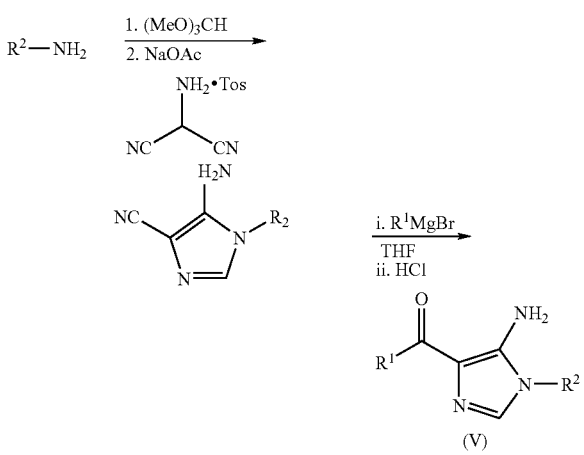

D. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with p38 kinase, including p38α kinase activity, or in which p38 kinase is implicated, in a pharmaceutically acceptable carrier. Diseases or disorders associated with p38 kinase include, but are not limited to, inflammatory diseases, autoimmune diseases, destructive bone disorders, proliferative disorders, angiogenic disorders, infectious diseases, neurodegenerative diseases, and viral diseases. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with p38 kinase activity or in which p38 kinase activity is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein (see, e.g., EXAMPLE 15) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with p38 kinase activity or in which p38 kinase activity is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating the activity of p38 kinase, or for treatment, prevention or amelioration of one or more symptoms of p38 kinase mediated diseases or disorders, or diseases or disorders in which p38 kinase activity, is implicated, within the packaging material, and a label that indicates that the compound or composition, or pharmaceutically acceptable derivative thereof, is used for modulating the activity of p38 kinase, or for treatment, prevention or amelioration of one or more symptoms of p38 kinase mediated diseases or disorders, or diseases or disorders in which p38 kinase is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which p38 kinase is implicated as a mediator or contributor to the symptoms or cause.

E. Evaluation of the Activity of the Compounds

Standard physiological, pharmacological and biochemical procedures are available for testing the compounds to identify those that possess biological activities that modulate the activity of cytokines, including the p38 kinase activity.

Compound inhibitory activity was measured in a radioactive enzyme assay. The buffer composition was adopted from Lisnock et al (Biochemistry, 1998, vol. 37, pp 16573-16581). Peptide substrate was selected from Chen et al (Biochemistry, 2000, vol. 39, 2079-2087). The concentrations of p38α, [γ-$^{33}$P-ATP] and peptide were equal 1 nM, 85 uM and 250 uM, respectively. Incorporation of $^{33}$P into peptide was measured using absorption on filtermats with subsequent wash with 100 mM phosphoric acid followed by ethanol.

Other conditions for the p38α enzymatic assay were also described in literature. They either differed from the assay described in either buffer composition (Biochemistry, 2000, vol. 39, 2079-2087)), or substrate (Biochemistry, 1998, vol. 37, pp 16573-16581), or both (Protein Sci., 1998, vol. 7, pp. 2249-2255).

F. Methods of Use of the Compounds and Compositions

In certain embodiments, the compounds provided herein are selective inhibitors of p38 kinase activity, and in one embodiment, the compounds are inhibitors of isoforms of p38 kinase, including, but not limited to p38α and p38βkinases. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α.

In view of their activity as inhibitors of p38α/β kinase, compounds of Formula (I) are useful in treating p38 associated conditions including, but not limited to, inflammatory diseases, autoinunune diseases, destructive bone disorders, proliferative disorders, angiogenic disorders, infectious diseases, neurodegenerative diseases, and viral diseases.

Inflammatory diseases related to p38-associated condition include, but are not limited to acute pancreatitis, chronic pancreatitis, asthma, allergies, and adult respiratory distress syndrome.

Autoimmune diseases related to p38-associated condition include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders related to p38-associated condition include, but are not limited to, osteoporosis, osteoarthritis and multiple myeloma-related bone disorder.

Proliferative diseases which are related to p38-associated condition include, but are not limited to, acute myelogenous leukemia, chronic myelogenous leukemia, metastatic melanoma, Kaposi's sarcoma, and multiple myeloma.

Infectious diseases related to p38-associated condition include, but are not limited to, sepsis, septic shock, and Shigellosis.

Viral diseases related to p38-associated condition include, but are not limited to, acute hepatitis infection (including hepatitis A, hepatitis B and hepatitis C), HIV infection and CMV retinitis.

Degenerative or diseases related to p38-associated condition include, but are not limited to, Alzheimer's disease, Parkinson's disease, cerebral ischemia, and other neurodegenerative diseases.

"p38-associated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors provided herein are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, cancer pain, dental pain and arthritis pain.

The diseases that may be treated or prevented by the p38 inhibitors provided herein, may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscel degeneration, cachexia, psoriatic arthritis, Reiter's syndrome, gout, traumatic arthritis, rubella arthritis, acute synovitis, diabetes, pancreatic beta.-cell disease and Alzheimer's disease.

TNF-mediated disease or condition includes, rheumatoid arthritis, rheumatoid spndylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and vetinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated disease or conditon includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds provided herein may be used topically to treat or prevent conditions caused or exacerbated by IL-1 or TNF. Such conditions include inflamed joints, eczema, psoriasis, inflammatory skin conditions such as sunburn, inflammatory eye conditions such as conjuctivitis, pyresis, pain and other conditions associated with inflammation.

In one embodiment, the specific conditions or diseases that may be treated with the compounds provided herein include, but are not limited to, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The compounds provided herein also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

G. Combination Therapy

Also provided herein are methods treating p38 kinase-associated conditions by administering to a subject in need thereof an effective amount of compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo (1,2-A) quinoxalines as disclosed in U.S. Pat. No. 4,200,750 and in S. Ceccarelli et al, "Imidazo(1,2-a)quinoxalin-4-amines: A Novel Class of Nonxanthine $A_1$ Adenosine Receptor Antagonists," *European Journal of Medicinal Chemistry* Vol. 33, (1998), at pp. 943-955; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds provided herein, may be used, for example, in those amounts indicated in the Physicians' Desk Reference (PDR) or as otherwise determined by one of ordinary skill in the art. In the methods provided herein, such other therapeutic agent(s) may be administered prior to, simultaneously with, or following the administration of the compounds provided herein.

The following examples are provided for illustrative purposes only and are not intended to limit the scope of the invention. Abbreviations employed in the Examples are defined herein. Compounds of the Examples are identified by the example and step in which they are prepared (for example, "1A" denotes the title compound of step A of Example 1), or by the example only where the compound is the title compound of the example (for example, "2" denotes the title compound of Example 2).

General Methods. Mass spectral data were obtained on a Thermo Finnigan LCQ Duo Ion Trap mass spectrometer. HPLC data were obtained on a $C_{18}$ Betasol column (2.1×50 mm) using gradient elution 10-90% (solvent A, acetonitrile+0.025% v TFA; solvent B, water+0.025% v TFA) over 4 minutes (flow rate 0.50 mL/min). Purification by preparatory HPLC on a Thermo Hypersi-Keystone Betasil C18 column 250×21.2 mm, particle size 5 μm, mobile phase: A, water+0.025% TFA; B, acetonitrile+0.025% TFA; gradient from 40 to 70% B; flow rate 15 mL/min.

EXAMPLE 1

Preparation of N-Cyclopropyl-4-methyl-3-(4-phenyl-pyrazolo[3,4-d]pyrimidin-1-yl)-benzamide

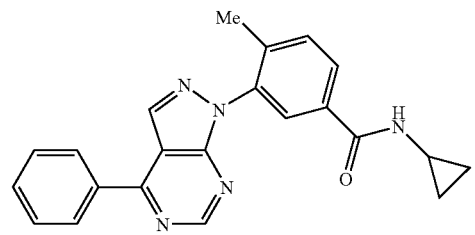

A. 3-Amino-N-cyclopropyl-4-methyl-benzamide

To a mixture of 3-amino-4-methyl-benzoic acid (10.2 g, 67.5 mmol) and cyclopropyl amine (9.33 mL, 135.0 mmol, 2 eq) in DMF (150 mL) was added EDCI (15.5 g, 81 mmol, 1.2 eq) followed by DMAP (cat.) at RT. The reaction was stirred overnight at RT, then concentrated. The residue was redissolved in water and extracted with EtOAc. The organic layer was washed with aqueous NaCl solution, dried over $Na_2SO_4$, and concentrated. The crude product was purified by flash chromatography on silica gel (gradient elution: 1:1 EtOAc/hexanes then 100% EtOAc) to provide 1A as a solid (9.5 g, 72%).

B. N-Cyclopropyl-3-hydrazino-4-methyl-benzamide

To a stirred solution of 3-Amino-N-cyclopropyl-4-methyl-benzamide (52 mg, 0.27 mmol) in water (3 ml) at 0° C. was added conc. HCl (3 mL) followed by the addition of sodium nitrite (20 mg, 0.30 mmol). The reaction mixture was stirred at 0° C. for 40 min then a solution of tin(II)chloride (114 mg, 0.61 mmol) in conc. HCl (1 mL) was added and the mixture was stirred for 1 hr then allowed to stand at −20° C. for 20 hr before it was warmed to RT. It was neutralized with $Na_2CO_3$ solution and extracted with $CH_2Cl_2$ six times. The combined extracts were dried over $Na_2SO_4$, concentrated, and the resulting solid was used without further purification. HPLC $t_R$ 1.06 min; MS m/z 205.9 [M+H]$^+$.

C. 3-(5-Amino-4-benzoyl-pyrazol-1-yl)-N-cyclopropyl-4-methyl-benzamide

To a stirred solution of hydrazine 1B in EtOH (10 ml) was added 2-benzoyl-3-phenylaminoacrylonitrile (676 mg, 0.27 mmol, preparation: Grothaus, J. Am. Chem. Soc. 58, 1334 (1936)) and mixture was heated (bath T=65-70° C.) for 16 hr. The mixture was cooled to RT, concentrated and purified by flash chromatography, eluting with 1:1 EtOAc/hexanes to remove impurities then 8:2 EtOAc/hexanes to give the title compound as an off-white solid (18 mg, 0.05 mmol, 19%). HPLC $t_R$ 2.11 min; MS m/z 361.1 [M+H]$^+$; $^1$H NMR (CD$_3$OD, 300 MHz) □ 7.92 (d, J=7.6, 1 H), 7.81 (m, 4 H), 7.54 (m, 4 H), 2.85 (m, 1 H), 2.22 (s, 3 H), 0.80 (d, J=5.7, 2H), 0.63 (s, 2 H) ppm; $^{13}$C NMR (CD$_3$OD, 75 MHz) □ 191.2, 170.1, 153.8, 143.3, 142.0, 141.1, 136.9, 134.8, 132.9, 132.7, 130.1, 129.7, 129.2, 128.1, 104.8, 24.1, 17.7, 6.6 ppm.

D. N-Cyclopropyl-4-methyl-3-(4-phenyl-pyrazolo[3,4-d]pyrimidin-1-yl)-benzamide

The mixture of 3-(5-Amino-4-benzoyl-pyrazol-1-yl)-N-cyclopropyl-4-methyl-benzamide (72 mg, 0.20 mmol), formamide (1.0 mL, excess), and acetic acid (0.2 mL) was heated in the microwave at 160° C. for 20 min. After cooling, the mixture was diluted with $CH_2Cl_2$ and water, and the $CH_2Cl_2$ layer was separated, dried over $Na_2SO_4$, filtered and concentrated. The crude product was purified by preparatory HPLC to provide the title compound (46 mg, 62%) as a white solid. HPLC $t_R$=2.3 min; MS m/z 370.3 [M+H]$^+$.

The following compounds were prepared in analogous fashion from the appropriately substituted starting materials:

TABLE 1

| Example | Structure | Name | MS [M+H]$^+$ | HPLC $t_R$ (min) |
|---|---|---|---|---|
| 1D-2 | 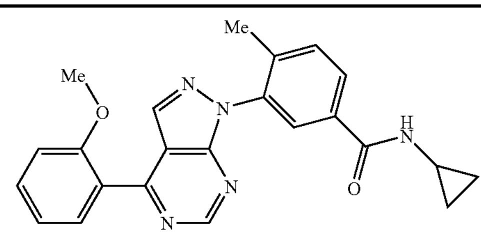 | N-Cyclopropyl-3-[4-(2-methoxy-phenyl)-pyrazolo[3,4-d]pyrimidin-1-yl]-4-methyl-benzamide | 400.3 | 2.2 |
| 1D-3 | 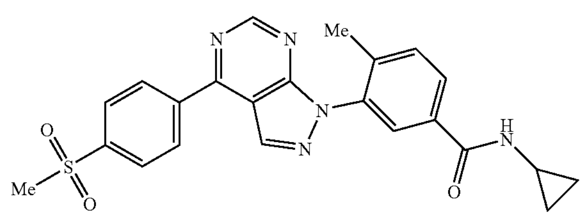 | N-Cyclopropyl-3-[4-(4-methanesulfonyl-phenyl)-pyrazolo[3,4-d]pyrimidin-1-yl]-4-methyl-benzamide | 448.2 | 2.03 |
| 1D-4 | 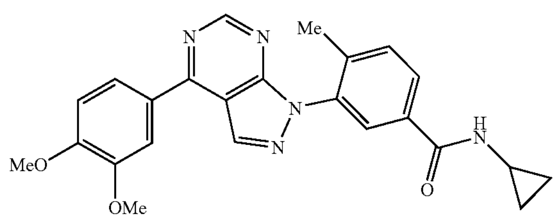 | N-Cyclopropyl-3-[4-(3,4-dimethoxy-phenyl)-pyrazolo[3,4-d]pyrimidin-1-yl]-4-methyl-benzamide | 430.3 | 2.16 |
| 1D-5 | 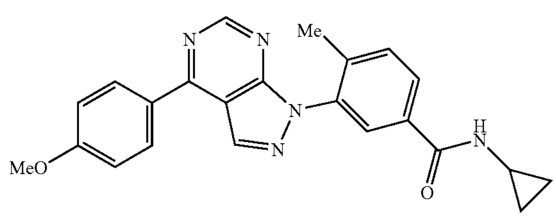 | N-Cyclopropyl-3-[4-(3-iodo-phenyl)-pyrazolo[3,4-d]pyrimidin-1-yl]-4-methyl-benzamide | 496.2 | |

TABLE 1-continued

| Example | Structure | Name | MS [M+H]+ | HPLC $t_R$ (min) |
|---|---|---|---|---|
| 1D-6 | 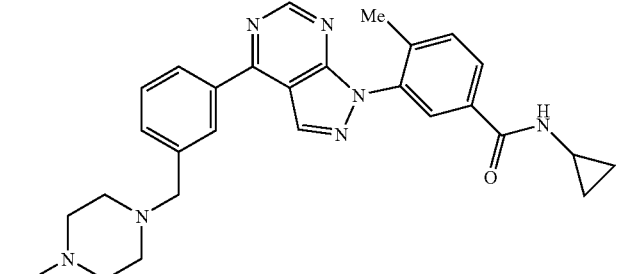 | N-Cyclopropyl-4-methyl-3-{4-[3-(4-methyl-piperazin-1-ylmethyl)-phenyl]-pyrazolo[3,4-d]pyrimidin-1-yl}-benzamide | 482.3 | 1.87 |
| 1D-7 | 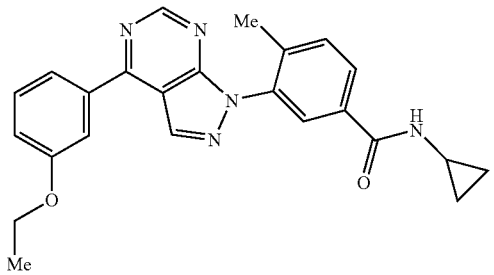 | N-Cyclopropyl-3-[4-(3-ethoxy-phenyl)-pyrazolo[3,4-d]pyrimidin-1-yl]-4-methyl-benzamide | 414.3 | 2.51 |
| 1D-8 | 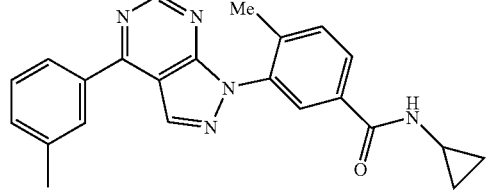 | N-Cyclopropyl-3-[4-(3-iodo-phenyl)-pyrazolo[3,4-d]pyrimidin-1-yl]-4-methyl-benzamide | | 2.71 |
| 1D-9 | 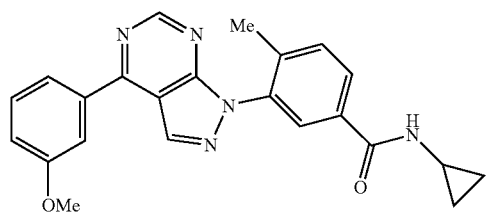 | N-Cyclopropyl-3-[4-(3-methoxy-phenyl)-pyrazolo[3,4-d]pyrimidin-1-yl]-4-methyl-benzamide | 400.2 | 2.28 |
| 1D-10 | 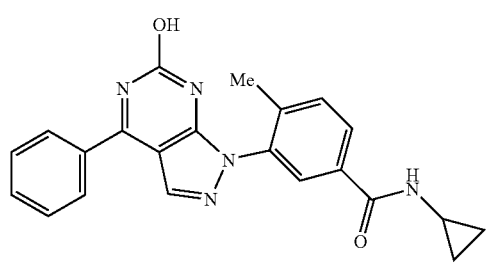 | N-Cyclopropyl-3-(6-hydroxy-4-phenyl-pyrazolo[3,4-d]pyrimidin-1-yl)-4-methyl-benzamide | | |
| 1D-11 | 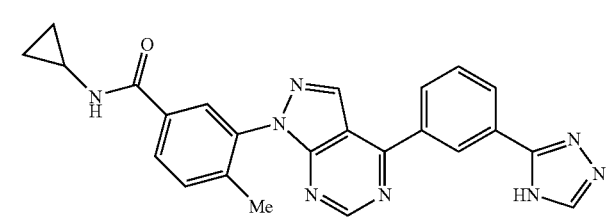 | N-Cyclopropyl-4-methyl-3-{4-[3-(4H-[1,2,4]triazol-3-yl)-phenyl]-pyrazolo[3,4-d]pyrimidin-1-yl}-benzamide | 437.2 | 1.83 |

TABLE 1-continued

| Example | Structure | Name | MS [M+H]+ | HPLC $t_R$ (min) |
|---|---|---|---|---|
| 1D-12 | 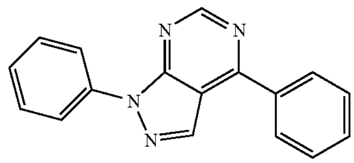 | 1,4-Diphenyl-1H-pyrazolo[3,4-d]pyrimidine | 273.26 | 3.08 |

EXAMPLE 2

Preparation of N-Cyclopropyl-4-methyl-3-(6-phenyl-purin-9-yl)-benzamide

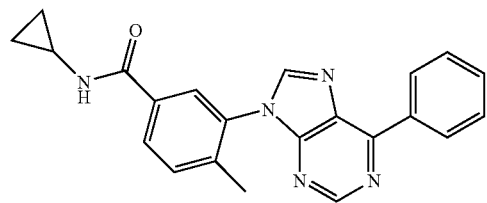

A. 3-(5-Amino-4-cyano-imidazol-1-yl)-N-cyclopropyl-4-methyl-benzamide

A mixture of 3-amino-N-cyclopropyl-4-methyl-benzamide (380 mg, 2.0 mmol, see Example 1A) in 2.0 mL of triethyl orthoformate was stirred at 120° C. in microwave for 20 minutes. The solvent was removed under reduced pressure. The residue was redissolved in 5 mL of acetic acid and then aminomalononitrile p-toluenesulfonate (506 mg, 2.0 mmol) and sodium acetate (164 mg, 2.0 mmol) were added. The reaction mixture was stirred at room temperature overnight. The mixture was diluted with 20 mL of water and the pH was adjusted to 8.0 with aqueous NaOH. The resulting mixture was extracted with EtOAc (3×50 mL). The combined organic layers were washed with water (10 mL) and brine (10 mL), dried over MgSO₄, filtered and concentrated in vacuo. The residue was purified by silica gel column chromatography (10/1, methylene chloride/methanol) to give 2A as a colorless solid (170 mg, 30%). HPLC $t_R$=1.39 min; MS m/z 282 [M+H]⁺.

B. 3-(5-Amino-4-benzoyl-imidazol-1-yl)-N-cyclopropyl-4-methyl-benzamide

To a solution of 3-(5-amino-4-cyano-imidazol-1-yl)-N-cyclopropyl-4-methyl-benzamide (56.4 mg, 0.2 mmol) in dry THF (10 ml) under nitrogen was added a 1 M solution of phenylmagnesium bromide in THF (1 mL, excess) at room temperature. After 1 h, a 3 N solution of HCl (10 ml) was added and the mixture was stirred overnight. The solution was neutralized with dilute aqueous NaOH. The mixture was extracted with ethyl acetate (2×100 mL), washed with water and dried over Na₂SO₄, and concentrated. The crude product was purified by HPLC to give 3B as a while solid (56 mg, 78%). HPLC $t_R$=2.07 min; MS m/z 361.17 [M+H]⁺.

C. N-Cyclopropyl-4-methyl-3-(6-phenyl-purin-9-yl)-benzamide

The mixture of 3-(5-amino-4-benzoyl-imidazol-1-yl)-N-cyclopropyl-4-methyl-benzamide (33 mg, 0.09 mmol), formamide (0.5 mL, excess), and acetic acid (0.1 mL) was heated in the microwave at 200° C. for 20 min. After cooling, the mixture was diluted with CH₂Cl₂ and water, and the CH₂Cl₂ layer was separated, dried over Na₂SO₄, filtered and concentrated. The crude product was purified by preparatory HPLC to provide the title compound (20 mg, 59%) as a white solid: HPLC $t_R$=2.20 min; MS m/z 370.3 [M+H]⁺.

The following compounds were prepared in analogous fashion from the appropriately substituted starting materials:

TABLE 2

| Example | Structure | Name | MS [M+H]+ | HPLC $t_R$ (min) |
|---|---|---|---|---|
| 2C-2 | 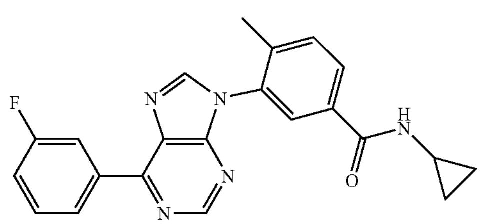 | N-Cyclopropyl-3-[6-(3-fluoro-phenyl)-purin-9-yl]-4-methyl-benzamide | 388.2 | 2.47 |

TABLE 2-continued

| Example | Structure | Name | MS [M+H]+ | HPLC $t_R$ (min) |
|---|---|---|---|---|
| 2C-3 | 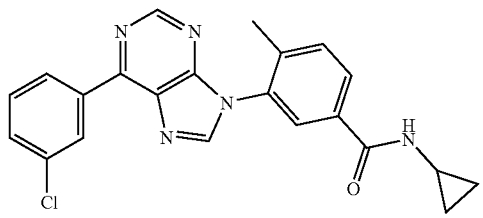 | 3-[6-(3-Chloro-phenyl)-purin-9-yl]-N-cyclopropyl-4-methyl-benzamide | 404.40 | 2.68 |
| 2C-4 | 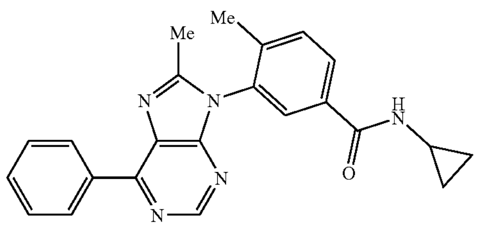 | N-Cyclopropyl-4-methyl-3-(8-methyl-6-phenyl-purin-9-yl)-benzamide | 384 | 2.17 |

EXAMPLE 3

Preparation of N-Cyclopropyl-4-methyl-3-[6-(4-mercaptophenyl)-purin-9-yl]-benzamide

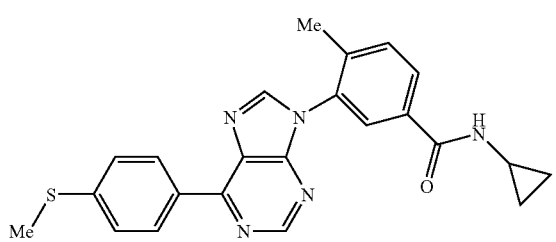

A. 3-(5-Amino-4-cyano-imidazol-1-yl)-N-cyclopropyl-4-methyl-benzamide

A mixture of 3-amino-N-cyclopropyl-4-methyl-benzamide (380 mg, 2.0 mmol) in 2.0 mL of triethyl orthoformate was stirred at 120° C. in microwave for 20 minutes. The solvent was removed under reduced pressure. The residue was dissolved in 5 mL of acetic acid and then was added aminomalononitrile p-toluenesulfonate (506 mg, 2.0 mmol) and sodium acetate (164 mg, 2.0 mmol). The reaction mixture was stirred at room temperature overnight. The mixture was diluted with 20 mL of water and the resulting precipitate was filtered to give 3-(5-amino-4-cyano-imidazol-1-yl)-N-cyclopropyl-4-methyl-benzamide 3A as a colorless solid (170 mg, 30%). HPLC $t_R$=1.39 min; MS m/z 282 [M+H]+.

B. 3-(5-Amino-4-benzoyl-imidazol-1-yl)-N-cyclopropyl-4-methyl-benzamide

To a solution of 3-(5-amino-4-cyano-imidazol-1-yl)-N-cyclopropyl-4-methyl-benzamide (100 mg, 0.36 mmol) in dry THF (15 ml) under nitrogen was added a 0.5 M solution of 4-mercaptophenylmagnesium bromide in THF (5 mL, excess) at room temperature. After 1 h, a 3 N solution of HCl (10 ml) was added and the mixture was stirred overnight. The solution was neutralized with dilute aqueous NaOH. The mixture was extracted with ethyl acetate (2×100 mL), washed with water, dried over $Na_2SO_4$, and concentrated. The crude product was purified by HPLC to give 3B as a while solid.

C. N-Cyclopropyl-4-methyl-3-[6-(4-mercaptophenyl)-purin-9-yl]-benzamide

The mixture of 3-[5-Amino-4-(4-mercapto-benzoyl)-imidazol-1-yl]-N-cyclopropyl-4-methyl-benzamide (33 mg, 0.09 mmol), formamide (0.5 mL, excess), and p-tolunesolfonic acid (10 mg) was heated in the microwave at 180° C. for 30 min. After cooling, the mixture was diluted with EtOAc and water, and the EtOAc layer was separated, dried over $Na_2SO_4$, filtered and concentrated. The crude product was purified by preparatory HPLC to provide the title compound (20 mg, 59%) as a white solid: HPLC $t_R$=2.47 min; MS m/z 416.27 [M+H]+.

The following compounds were prepared in analogous fashion from the appropriately substituted starting materials:

TABLE 3

| Example | Structure | Name | MS [M+H]+ | HPLC $t_R$ (min) |
|---|---|---|---|---|
| 3C-2 | 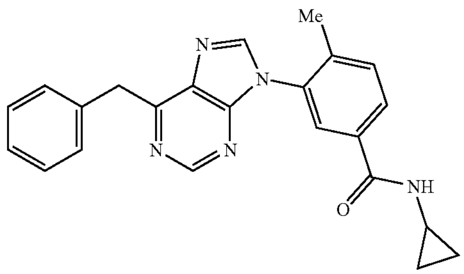 | 3-(6-Benzyl-4,5-dihydro-purin-9-yl)-N-cyclopropyl-4-methyl-benzamide | 384.29 | 2.40 |
| 3C-3 | 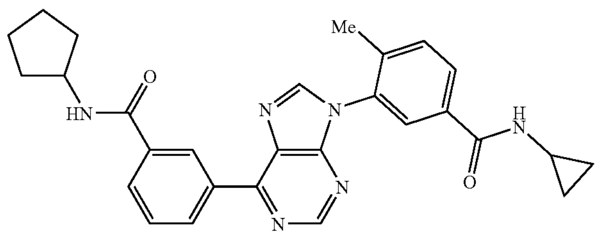 | 3-[6-3-Cyclopentylcarbamoyl-phenyl)-purin-9-yl]-N-cyclopropyl-4-methyl-benzamide | 481.23 | 2.08 |
| 3C-4 | 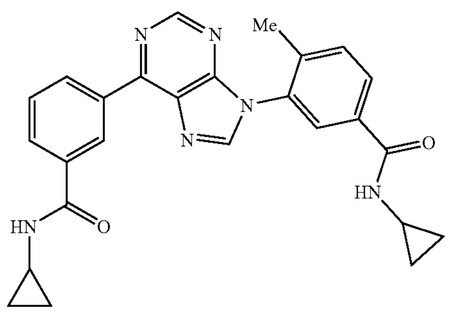 | N-Cyclopropyl-3-[6-(3-cyclopropylcarbamoyl-phenyl)-purin-9-yl]-4-methyl-benzamide | 453.19 | 1.90 |
| 3C-5 | 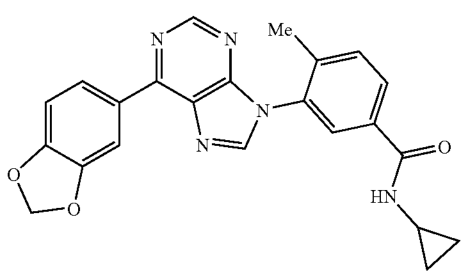 | 3-(6-Benzo[1,3]dioxol-5-yl-purin-9-yl)-N-cyclopropyl-4-methyl-benzamide | 414.23 | 2.22 |
| 3C-6 | 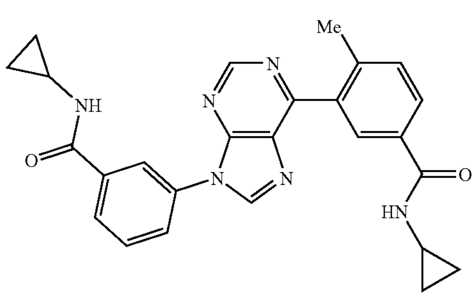 | N-Cyclopropyl-3-[9-(3-cyclopropylcarbamoyl-phenyl)-9H-purin-6-yl]-4-methyl-benzamide | 453.18 | 1.80 |

TABLE 3-continued

| Example | Structure | Name | MS [M+H]+ | HPLC $t_R$ (min) |
|---|---|---|---|---|
| 3C-7 | 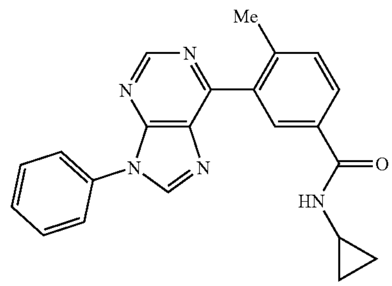 | N-Cyclopropyl-4-methyl-3-(9-phenyl-9H-purin-6-yl)-benzamide | 370.12 | 2.06 |
| 3C-8 | 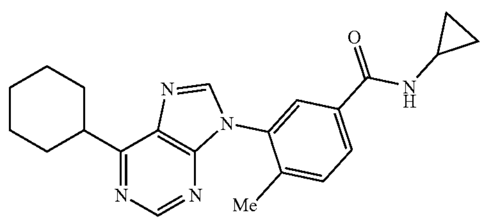 | 3-(6-Cyclohexyl-purin-9-yl)-N-cyclopropyl-4-methyl-benzamide | 376.36 | 2.19 |
| 3C-9 | 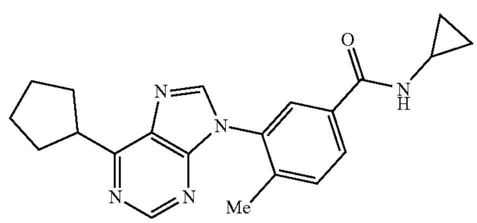 | 3-(6-Cyclopentyl-purin-9-yl)-N-cyclopropyl-4-methyl-benzamide | 362.31 | 2.07 |

EXAMPLE 4

Preparation of N-Cyclopropyl-3-[6-(3-methanesulfonylamino-phenyl)-purin-9-yl]-4-methyl-benzamide

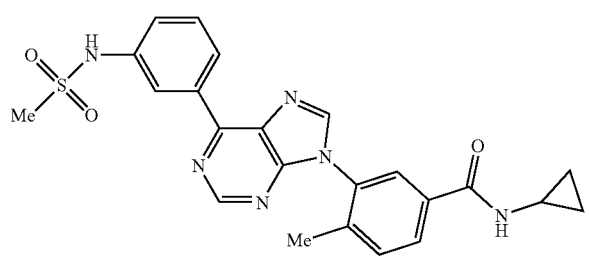

A. 3-(5-Amino-6-chloro-pyrimidin-4-ylamino)-N-cyclopropyl-4-methyl-benzamide

To a mixture of 4,6-dichloro-pyrimidin-5-ylamine (328 mg, 2.0 mmol) and 3-amino-N-cyclopropyl-4-methyl-benzamide (760 mg, 4.0 mmol) in NMP (1.5 ml) was added N,N-diisopropylethyl amine (348 µl, 2.0 mmol). The reaction mixture was heated with microwave at 220° C. for 30 minutes. It was then cooled to RT and purified by a flash chromatography, eluting with 3:1 EtOAc/hexanes to give the compound 4A as an off-white solid (267 mg, 0.84 mmol, 42%). HPLC $t_R$=1.59 min; MS m/z 318 [M+H]+; $^1$H NMR (300 MHz, CD$_3$OD) δ 0.64-0.68 (m, 2H), 0.80-0.84 (m, 2H), 2.23 (s, 3H), 2.83-2.87 (m, 1H), 7.40 (d, J=7.9, 1H), 7.66 (d, J=7.9, 1H). 7.80 (m, 2H) ppm.

B. 3-(6-Chloro-purin-9-yl)-N-cyclopropyl-4-methyl-benzamide

The mixture of 3-(5-amino-6-chloro-pyrimidin-4-ylamino)-N-cyclopropyl-4-methyl-benzamide (420 mg, 1.32 mmol) in triethyl orthoformate (1 ml) and acetic acid (3 drops) was heated with microwave at 120° C. for 15 minutes. It was cooled to room temperature and purified by a column chromatography eluting with 1:1 EtOAc/hexanes to give compound 4B as a white solid (350 mg, 1.07 mmol, 81%). HPLC $t_R$=2.07 min; MS m/z 328 [M+H]+; $^1$H NMR (300 MHz, CD$_3$OD) δ 0.58-0.59 (m, 2H), 0.72-0.77 (m, 2H), 2.13 (s, 3H), 2.77-2.82 (m, 1H), 7.55 (d, J=7.9 Hz, 1H), 7.82 (s, 1H), 7.91 (d, J=7.9 Hz, 1H), 8.65 (s, 1H), 8.69 (s, 1H) ppm.

C. N-Cyclopropyl-3-[6-(3-methanesulfonylamino-phenyl)-purin-9-yl]-4-methyl-benzamide To a mixture of compound 4B (16 mg, 0.046 mmol), 3-methanesulfonylamino-boronic acid and Pd(Ph$_3$P)$_4$ (5.5 mg, 0.0048 mmol) was added 1,4-dioxane (0.2 ml) and sat. K$_2$CO$_3$ (0.1 ml). The resulting suspension was then heated with microwave at 120° C. for 10 minutes. It was then cooled to RT and purified by HPLC to give the title compound as a white solid (7.6 mg, 0.016 mmol, 33%). HPLC $t_R$=1.96 min; MS m/z 463 [M+H]$^+$; $^1$H NMR (300 MHz, CD$_3$OD) δ 0.64 (m, 2H), 0.79-0.82 (m, 2H), 2.21 (s, 3H), 2.84-2.88 (m, 1H), 3.08 (s, 3H), 7.47-7.62 (m, 3H), 7.89-7.98 (m, 2H), 8.57-8.68 (m, 3H), 8.95 (s, 1H) ppm.

The following compounds were prepared in analogous fashion from the appropriately substituted boronic acid:

TABLE 4

| Example | Structure | Name | MS [M+H]$^+$ | HPLC $t_R$ (min) |
|---|---|---|---|---|
| 4C-2 | 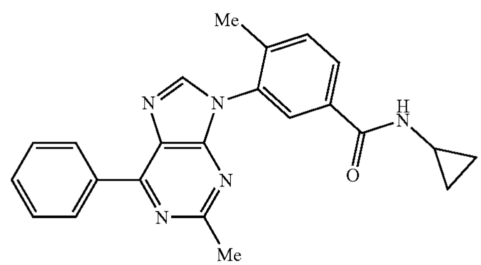 | N-Cyclopropyl-4-methyl-3-(2-methyl-6-phenyl-purin-9-yl)-benzamide | 384 | 2.39 |
| 4C-3 | 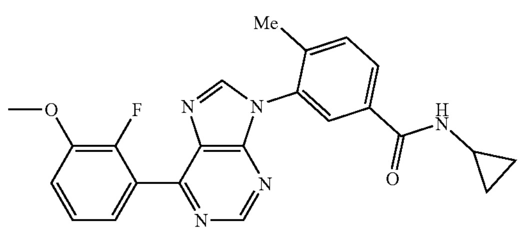 | N-Cyclopropyl-3-[6-(2-fluoro-3-methoxy-phenyl)-purin-9-yl]-4-methyl-benzamide | 418 | 2.04 |
| 4C-4 | 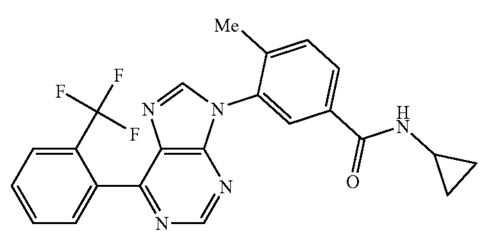 | N-Cyclopropyl-4-methyl-3-[6-(2-trifluoromethyl-phenyl)-purin-9-yl]-benzamide | 438 | 2.17 |
| 4C-5 | 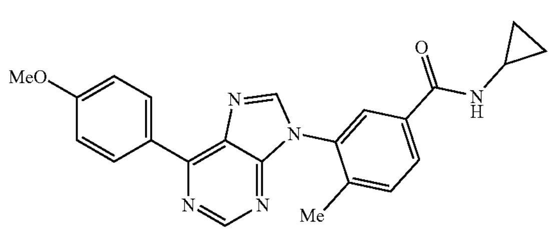 | N-Cyclopropyl-3-[6-(4-methoxy-phenyl)-purin-9-yl]-4-methyl-benzamide | 400.3 | 2.30 |
| 4C-6 | 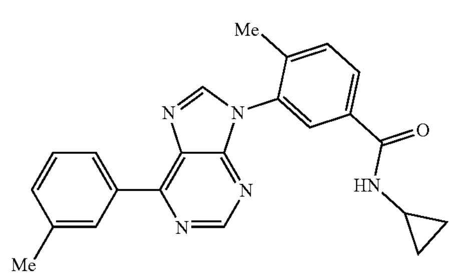 | N-Cyclopropyl-4-methyl-3-(6-m-tolyl-purin-9-yl)-benzamide | 384.28 | 2.45 |

TABLE 4-continued

| Example | Structure | Name | MS [M+H]+ | HPLC $t_R$ (min) |
|---|---|---|---|---|
| 4C-7 | 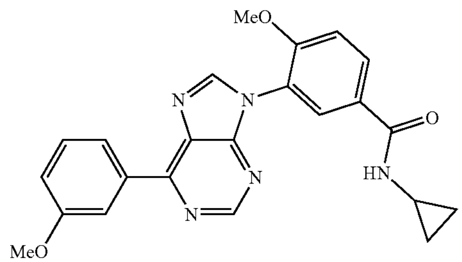 | N-Cyclopropyl-3-[6-(3-methoxy-phenyl)-purin-9-yl]-4-methyl-benzamide | 400.24 | 2.33 |
| 4C-8 | 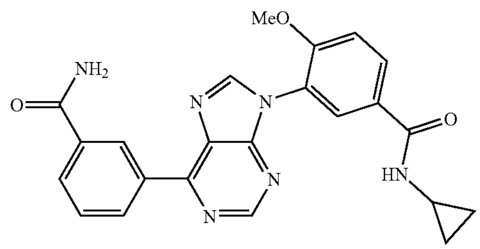 | 3-[6-(3-Carbamoyl-phenyl)-purin-9-yl]-N-cyclopropyl-4-methyl-benzamide | 413.13 | 1.71 |
| 4C-9 | 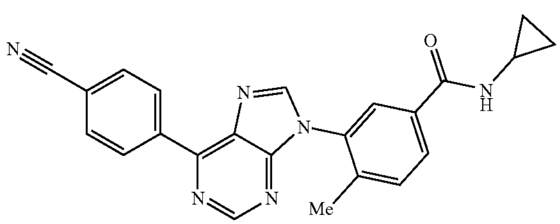 | 3-[6-(4-Cyano-phenyl)purin-9-yl]-N-cyclopropyl-4-methyl-benzamide | 395.2 | 2.29 |
| 4C-10 | 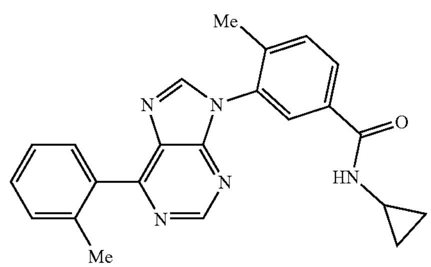 | N-Cyclopropyl-4-methyl-3-(6-o-tolyl-purin-9-yl)-benzamide | 384.3 | 2.16 |
| 4C-11 | 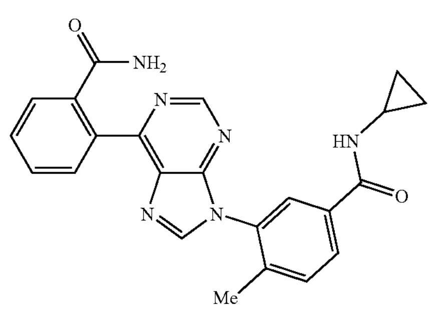 | 3-[6-(2-Carbamoyl-phenyl)-purin-9-yl]-N-cyclopropyl-4-methyl-benzamide | 413.13 | 1.53 |
| 4C-12 | 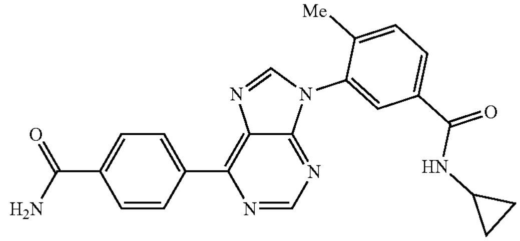 | 3-[6-(4-Carbamoyl-phenyl)-purin-9-yl]-N-cyclopropyl-4-methyl-benzamide | 413.27 | 1.66 |

TABLE 4-continued

| Example | Structure | Name | MS [M+H]+ | HPLC t_R (min) |
|---|---|---|---|---|
| 4C-13 | 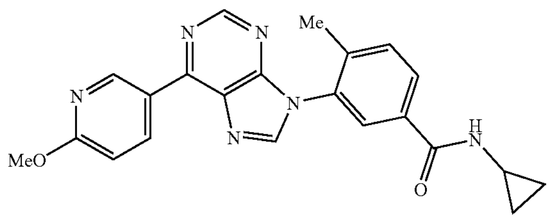 | N-Cyclopropyl-3-[6-(6-methoxy-pyridin-3-yl)-purin-9-yl]-4-methyl-benzamide | 401.00 | 2.26 |
| 4C-14 | 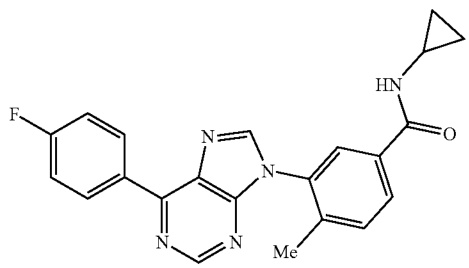 | N-Cyclopropyl-3-[6-(3-methanesulfonylamino-phenyl)-purin-9-yl]-4-methyl-benzamide | 463.00 | 1.96 |
| 4C-15 | 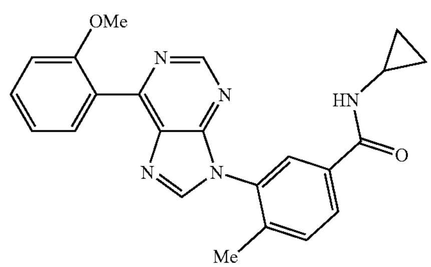 | N-Cyclopropyl-3-[6-(4-fluoro-phenyl)-purin-9-yl]-4-methyl-benzamide | 388.00 | 2.26 |
| 4C-16 | 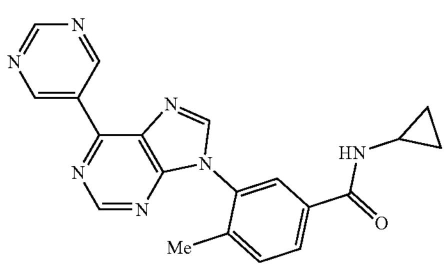 | N-Cyclopropyl-3-[6-(2-methoxy-phenyl)-purin-9-yl]-4-methyl-benzamide | 400.21 | 1.88 |
| 4C-17 | 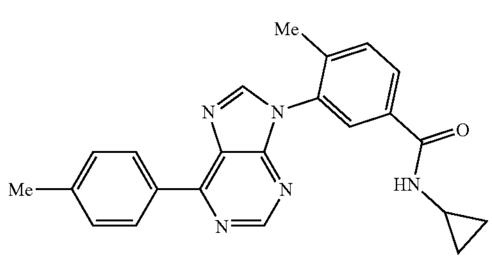 | N-Cyclopropyl-4-methyl-3-(6-pyrimidin-5-yl-purin-9-yl)-benzamide | 372.00 | 1.66 |
| 4C-18 | 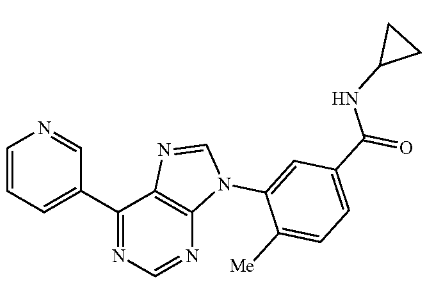 | N-Cyclopropyl-4-methyl-3-(6-p-tolyl-purin-9-yl)-benzamide | 384.25 | 2.47 |

TABLE 4-continued

| Example | Name | MS [M+H]+ | HPLC t_R (min) |
|---|---|---|---|
| 4C-19 | N-Cyclopropyl-4-methyl-3-(6-pyridin-3-yl-purin-9-yl)-benzamide | 371.00 | 1.56 |
| 4C-20 | N-Cyclopropyl-3-[6-(2-fluoro-phenyl)-purin-9-yl]-4-methyl-benzamide | 388.23 | 2.05 |
| 4C-21 | N-Cyclopropyl-3-[6-(3-cyclopropylcarbamoyl-6-methyl-phenyl)-purin-9-yl]-4-methyl-benzamide | 467.00 | 1.82 |
| 4C-22 | 3-[6-(3-Cyano-phenyl)-purin-9-yl]-N-cyclopropyl-4-methyl-benzamide | 395.2 | 2.30 |
| 4C-23 | 3-(8-Amino-6-phenyl-purin-9-yl)-N-cyclopropyl-4-methyl-benzamide | | |

TABLE 4-continued

| Example | Name | MS [M+H]+ | HPLC t$_R$ (min) |
|---|---|---|---|
| 4C-24 | 3-[6-(2-Cyano-phenyl)-purin-9-yl]-N-cyclopropyl-4-methyl-benzamide | 395.16 | 2.04 |
| 4C-25 | N-Cyclopropyl-3-[6-(2,4-difluoro-phenyl)-purin-9-yl]-4-methyl-benzamide | 406.00 | 2.26 |
| 4C-26 | N-Cyclopropyl-4-methyl-3-{6-[3-(4H-[1,2,4]triazol-3-yl)-phenyl]-purin-9-yl}-benzamide | 437.23 | 1.81 |
| 4C-27 | N-Cyclopropyl-3-[6-(2,3-dihydro-benzo[1,4]dioxin-6-yl)-purin-9-yl]-4-methyl-benzamide | 428.25 | 2.25 |
| 4C-28 | 3-[6-(2-Chloro-phenyl)-purin-9-yl]-N-cyclopropyl-4-methyl-benzamide | 404.00 | 2.20 |
| 4C-29 | 4-[9-(5-Cyclopropylcarbamoyl-2-methyl-phenyl)-9H-purin-6-yl]-benzoic acid methyl ester | 428 | 2.20 |

TABLE 4-continued

| Example | Structure | Name | MS [M+H]+ | HPLC $t_R$ (min) |
|---|---|---|---|---|
| 4C-30 | 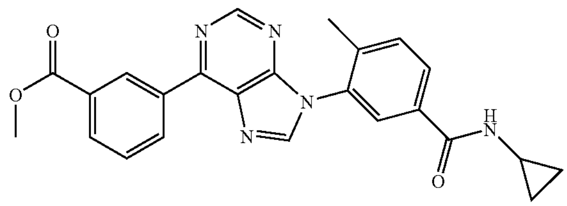 | 3-[9-(5-Cyclopropylcarbamoyl-2-methyl-phenyl)-9H-purin-6-yl]-benzoic acid methyl ester | 428 | 2.38 |
| 4C-31 | 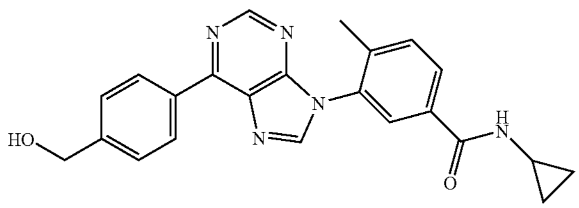 | N-Cyclopropyl-3-[6-(4-hydroxymethyl-phenyl)-purin-9-yl]-4-methyl-benzamide | 400 | 2.07 |
| 4C-32 | 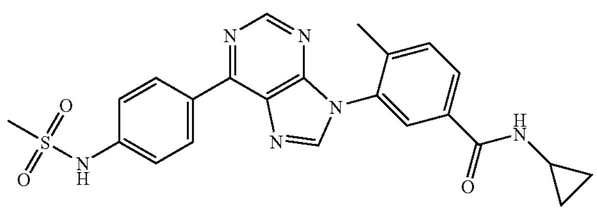 | N-Cyclopropyl-3-[6-(4-methanesulfonylamino-phenyl)-purin-9-yl]-4-methyl-benzamide | 463 | 2.14 |
| 4C-33 | 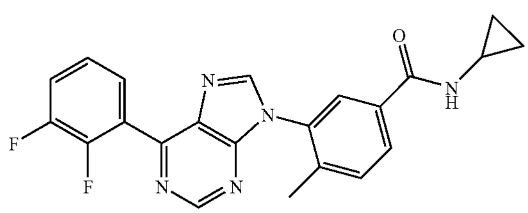 | N-Cyclopropyl-3-[6-(2,3-difluoro-phenyl)-purin-9-yl]-4-methyl-benzamide | 406 | 2.31 |
| 4C-34 | 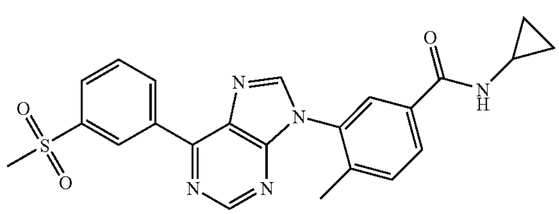 | N-Cyclopropyl-3-[6-(3-methanesulfonyl-phenyl)-purin-9-yl]-4-methyl-benzamide | 448 | 2.19 |
| 4C-35 | 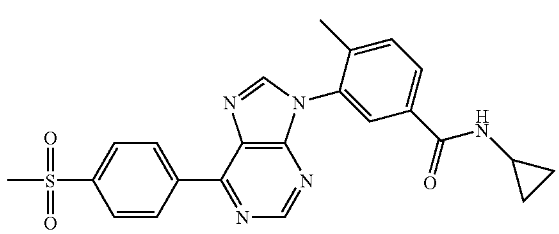 | N-Cyclopropyl-3-[6-(4-methanesulfonyl-phenyl)-purin-9-yl]-4-methyl-benzamide | 448 | 1.79 |

TABLE 4-continued

| Example | Structure | Name | MS [M+H]+ | HPLC $t_R$ (min) |
|---|---|---|---|---|
| 4C-36 | 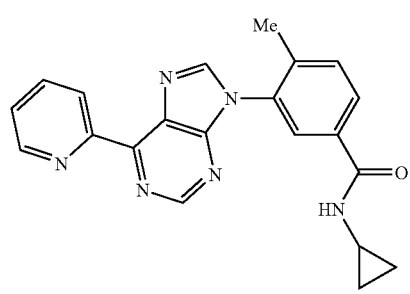 | N-Cyclopropyl-3-[6-(3-hydroxymethyl-phenyl)-purin-9-yl]-4-methyl-benzamide | 400 | 1.95 |

EXAMPLE 5

Preparation of N-Cyclopropyl-4-methyl-3-(6-pyridin-2-yl-purin-9-yl)-benzamide

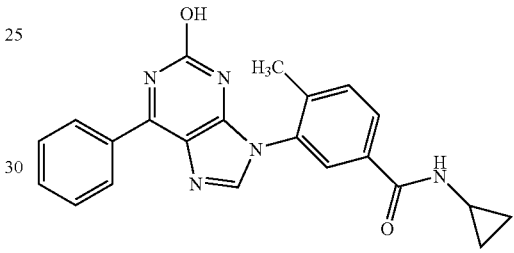

A mixture of 3-(6-chloro-purin-9-yl)-N-cyclopropyl-4-methyl-benzamide (16 mg, 0.049 mmol), Pd(PPh$_3$)$_4$ (5.7 mg, 0.0049 mmol) and the 2-tributylstannanyl-pyridine (36 mg, 0.098 mmol) was suspended in DMF (0.25 ml). The mixture was heated with microwave at 160° C. for 10 minutes. The mixture was purified by HPLC to give the desired product as a white solid (16 mg, 0.043 mmol, 88%). HPLC $t_R$=1.59 min; MS m/z 371 [M+H]+.

The following compounds were prepared in analogous fashion from the appropriately substituted organostannane:

Example 5-2, N-Cyclopropyl-4-methyl-3-(6-pyrimidin-2-yl-purin-9-yl)-benzamide, HPLC $t_R$=1.40 min; MS m/z 371.4 [M+H]+.

Example 5-3, N-Cyclopropyl-4-methyl-3-(6-pyrimidin-2-yl-purin-9-yl)-benzamide, HPLC $t_R$=1.40 min; MS m/z 372 [M+H]+.

Example 5-4, N-Cyclopropyl-4-methyl-3-(6-thiazol-2-yl-purin-9-yl)-benzamide, HPLC $t_R$=1.85 min; MS m/z 377 [M+H]+.

EXAMPLE 6

Preparation of N-Cyclopropyl-3-(2-hydroxy-6-phenyl-purin-9-yl)-4-methyl-benzamide

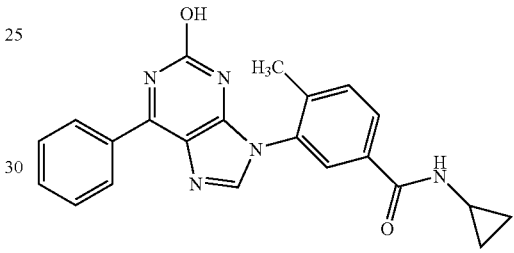

To a stirred solution of 3-(5-amino-4-benzoyl-imidazol-1-yl)-N-cyclopropyl-4-methyl-benzamide (9.2 mg, 0.026 mmol) in 0.3 mL acetic acid was added urea (20 mg) and the mixture was heated at 180° C. for 20 min. in the microwave. The crude product was purified by HPLC to give a colorless solid (2.4 mg, 24%). HPLC $t_R$=1.63 min; MS m/z 386 [M+H]+.

EXAMPLE 7

Preparation of N-Cyclopropyl-4-methyl-3-(6-phenylamino-purin-9-yl)-benzamide

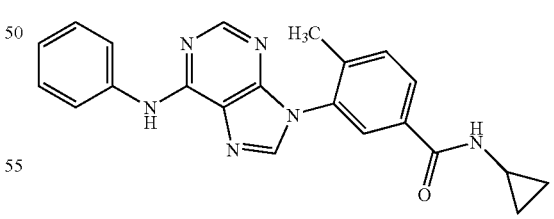

The mixture of 3-(6-chloro-purin-9-yl)-N-cyclopropyl-4-methyl-benzamide (10 mg, 0.029 mmol) and aniline (14 mg, 0.15 mmol) in 0.2 mL of dioxane was heated with microwave at 140° C. for 20 minutes. It was then cooled to RT and purified by HPLC give the title compound as an off-white solid (5.2 mg, 46%). HPLC $t_R$=2.09 min; MS m/z 385 [M+H]+.

The following compounds were prepared in analogous fashion from the appropriately substituted amine:

TABLE 5

| Example | Structure | Name | MS [M+H]+ | HPLC C $t_R$ (min) |
|---------|-----------|------|-----------|---------------------|
| 7-2 | 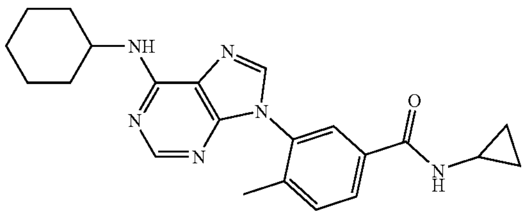 | 3-(6-Cyclohexylamino-purin-9-yl)-N-cyclopropyl-4-methyl-benzamide | 391 | 2.04 |
| 7-3 | 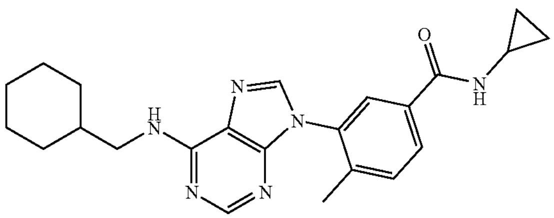 | 3-[6-(Cyclohexylmethyl-amino)-purin-9-yl]-N-cyclopropyl-4-methyl-benzamide | 405 | 2.35 |
| 7-4 | 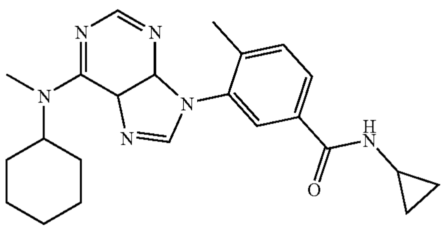 | 3-[6-(Cyclohexyl-methyl-amino)-purin-9-yl]-N-cyclopropyl-4-methyl-benzamide | 405 | 2.25 |
| 7-5 | 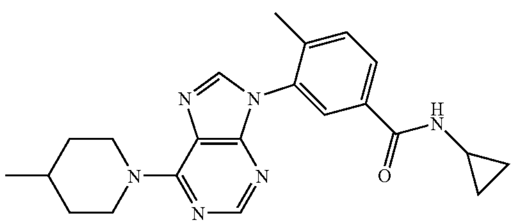 | N-Cyclopropyl-4-methyl-3-[6-(4-methyl-piperidin-1-yl)-purin-9-yl]-benzamide | 391 | 2.32 |
| 7-6 | 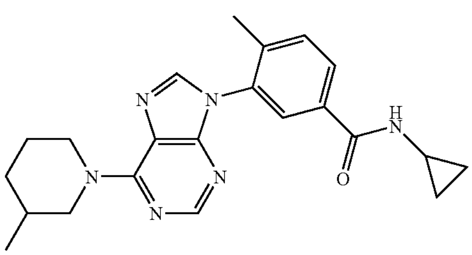 | N-Cyclopropyl-4-methyl-3-[6-(3-methyl-piperidin-1-yl)-purin-9-yl]-benzamide | 391 | 2.31 |
| 7-7 | 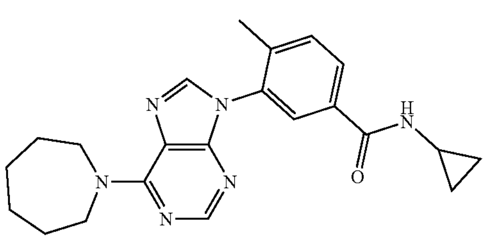 | 3-(6-Azocan-1-yl-purin-9-yl)-N-cyclopropyl-4-methyl-benzamide | 405 | 2.20 |

TABLE 5-continued

| Example | Name | MS [M+H]+ | HPLC C t$_R$ (min) |
|---|---|---|---|
| 7-8 | N-Cyclopropyl-4-methyl-3-(6-pyrrolidin-1-yl-purin-9-yl)-benzamide | 363 | 1.52 |
| 7-9 | 3-(6-Azepan-1-yl-purin-9-yl)-N-cyclopropyl-4-methyl-benzamide | 391 | 2.06 |
| 7-10 | 3-(6-Cyclopentylamino-purin-9-yl)-N-cyclopropyl-4-methyl-benzamide | 377 | 1.83 |
| 7-11 | N-Cyclopropyl-3-[6-(2,2-dimethyl-propylamino)-purin-9-yl]-4-methyl-benzamide | 379 | 2.01 |
| 7-12 | 3-(6-Cycloheptylamino-purin-9-yl)-N-cyclopropyl-4-methyl-benzamide | 405 | 2.21 |
| 7-13 | 3-[6-(Bicyclo[2.2.1]hept-2-ylamino)-purin-9-yl]-N-cyclopropyl-4-methyl-benzamide | 403 | 2.09 |

TABLE 5-continued

| Example | Structure | Name | MS [M+H]+ | HPLC C t_R (min) |
|---|---|---|---|---|
| 7-14 | 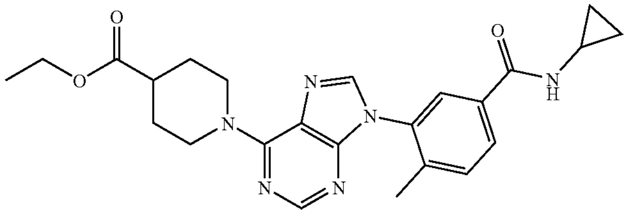 | 1-[9-(5-Cyclopropylcarbamoyl-2-methyl-phenyl)-9H-purin-6-yl]-piperidine-4-carboxylic acid ethyl ester | 449 | 2.31 |
| 7-15 | 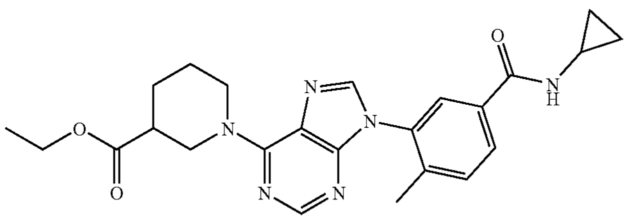 | 1-[9-(5-Cyclopropylcarbamoyl-2-methyl-phenyl)-9H-purin-6-yl]-piperidine-3-carboxylic acid ethyl ester | 449 | 2.36 |
| 7-16 | 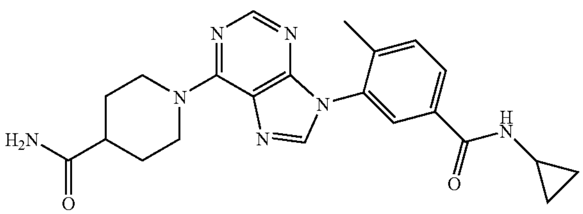 | 1-[9-(5-Cyclopropylcarbamoyl-2-methyl-phenyl)-9H-purin-6-yl]-piperidine-4-carboxylic acid amide | 420 | 1.29 |
| 7-17 | 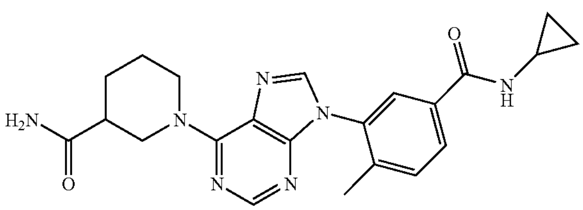 | 1-[9-(5-Cyclopropylcarbamoyl-2-methyl-phenyl)-9H-purin-6-yl]-piperidine-3-carboxylic acid amide | 420 | 1.36 |
| 7-18 | 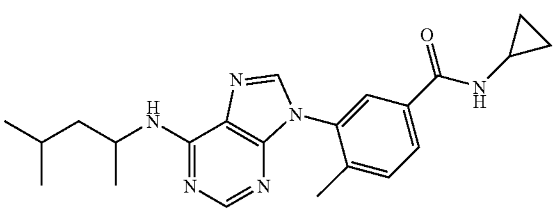 | N-Cyclopropyl-3-[6-(1,3-dimethyl-butylamino)-purin-9-yl]-4-methyl-benzamide | 393 | 2.19 |
| 7-19 | 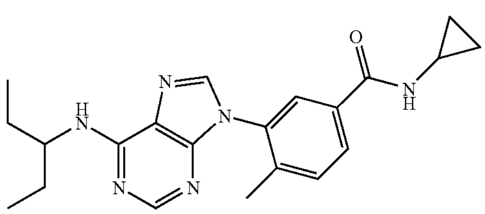 | N-Cyclopropyl-3-[6-(1-ethyl-propylamino)-purin-9-yl]-4-methyl-benzamide | 379 | 1.92 |
| 7-20 | 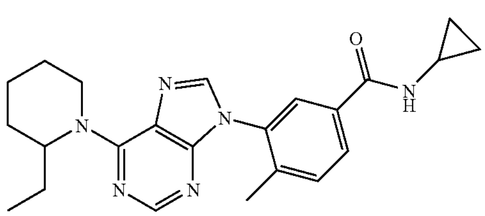 | N-Cyclopropyl-3-[6-(2-ethyl-piperidin-1-yl)-purin-9-yl]-4-methyl-benzamide | 405 | 2.45 |

TABLE 5-continued

| Example | Structure | Name | MS [M+H]+ | HPLC C t$_R$ (min) |
|---|---|---|---|---|
| 7-21 | 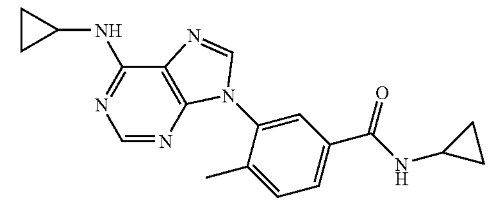 | N-Cyclopropyl-3-(6-cyclopropylamino-purin-9-yl)-4-methyl-benzamide | 349 | 1.46 |
| 7-22 | 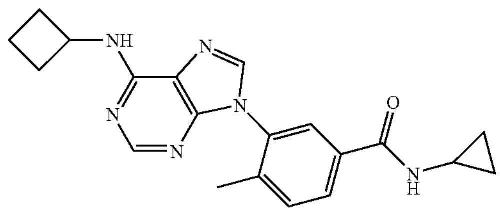 | 3-(6-Cyclobutylamino-purin-9-yl)-N-cyclopropyl-4-methyl-benzamide | 363 | 1.75 |
| 7-23 | 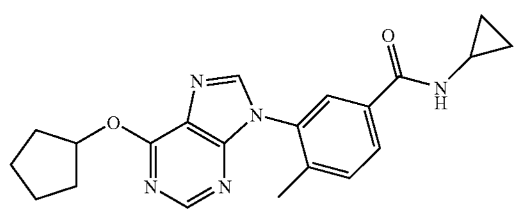 | 3-(6-Cyclopentyloxy-purin-9-yl)-N-cyclopropyl-4-methyl-benzamide | 378 | 2.4 |
| 7-24 | 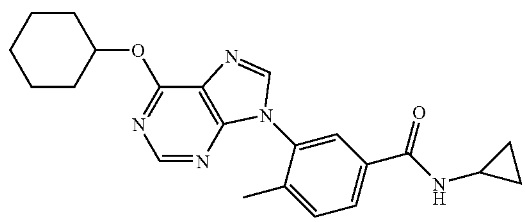 | 3-(6-Cyclohexyloxy-purin-9-yl)-N-cyclopropyl-4-methyl-benzamide | 392 | 2.59 |
| 7-25 | 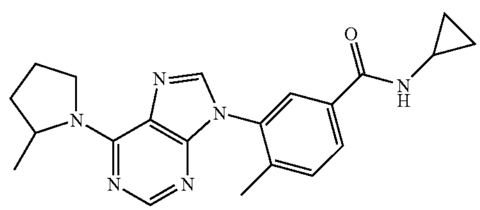 | N-Cyclopropyl-4-methyl-3-[6-(2-methyl-pyrrolidin-1-yl)-purin-9-yl]-benzamide | 377 | 2.33 |
| 7-26 | 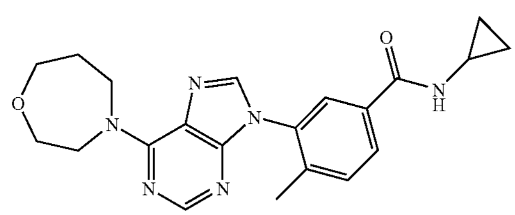 | N-Cyclopropyl-4-methyl-3-(6-[1,4]oxazepan-4-yl-purin-9-yl)-benzamide | 393 | 2.44 |
| 7-27 | 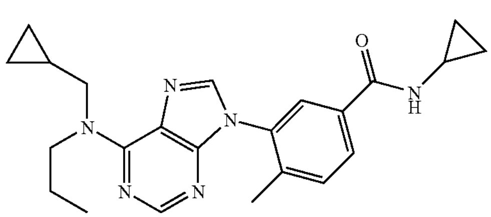 | N-Cyclopropyl-3-[6-(cyclopropylmethyl-propyl-amino)-purin-9-yl]-4-methyl-benzamide | 405 | 2.50 |

TABLE 5-continued

| Example | Structure | Name | MS [M+H]+ | HPLC C $t_R$ (min) |
|---|---|---|---|---|
| 7-28 | 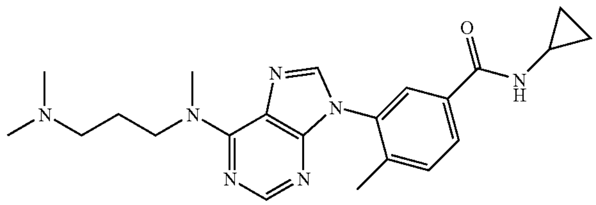 | N-Cyclopropyl-3-{6-[(3-dimethylamino-propyl)-methyl-amino]-purin-9-yl}-4-methyl-benzamide | 408 | 1.47 |
| 7-29 | 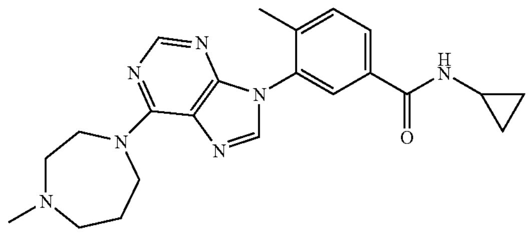 | N-Cyclopropyl-4-methyl-3-[6-(4-methyl-[1,4]diazepan-1-yl)-purin-9-yl]-benzamide | 406 | 1.59 |
| 7-30 | 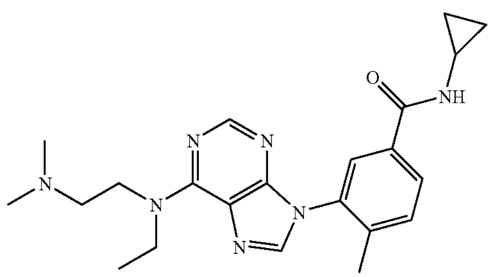 | N-Cyclopropyl-3-{6-[(2-dimethylamino-ethyl)-ethyl-amino]-purin-9-yl}-4-methyl-benzamide | 408 | 1.65 |
| 7-31 | 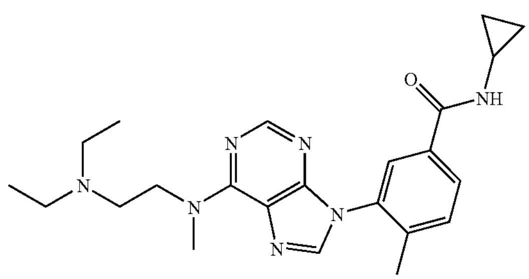 | N-Cyclopropyl-3-{6-[(2-diethylamino-ethyl)-methyl-amino]-purin-9-yl}-4-methyl-benzamide | 422 | 1.64 |
| 7-32 | 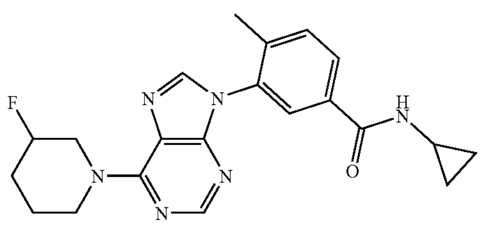 | N-Cyclopropyl-3-[6-(3-fluoro-piperidin-1-yl)-purin-9-yl]-4-methyl-benzamide | 395 | 2.12 |
| 7-33 | 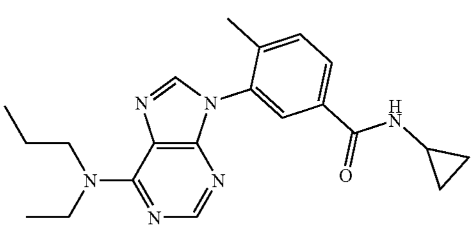 | N-Cyclopropyl-3-[6-(ethyl-propyl-amino)-purin-9-yl]-4-methyl-benzamide | 379 | 2.16 |

TABLE 5-continued

| Example | Structure | Name | MS [M+H]+ | HPLC C $t_R$ (min) |
|---|---|---|---|---|
| 7-34 | 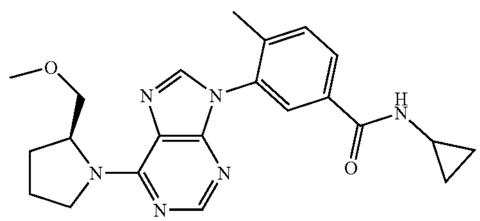 | N-Cyclopropyl-3-[6-(2-methoxymethyl-pyrrolidin-1-yl)-purin-9-yl]-4-methyl-benzamide | 407 | 1.96 |
| 7-35 | 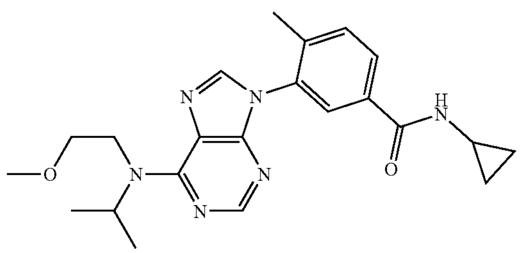 | N-Cyclopropyl-3-{6-[isopropyl-(2-methoxy-ethyl)-amino]-purin-9-yl}-4-methyl-benzamide | 409 | 2.16 |
| 7-36 | 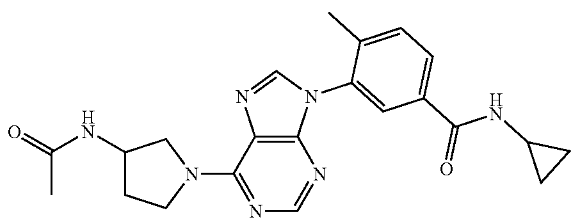 | 3-[6-(3-Acetylamino-pyrrolidin-1-yl)-purin-9-yl]-N-cyclopropyl-4-methyl-benzamide | 420 | 1.49 |
| 7-37 | 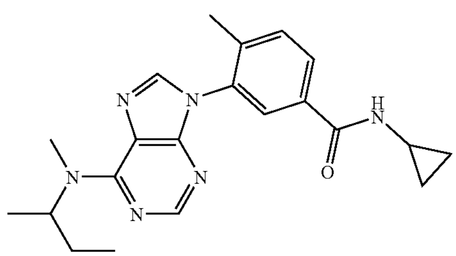 | 3-[6-(sec-Butyl-methyl-amino)-purin-9-yl]-N-cyclopropyl-4-methyl-benzamide | 379 | 2.16 |
| 7-38 | 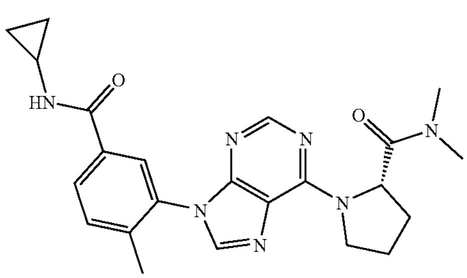 | 1-[9-(5-Cyclopropylcarbamoyl-2-methyl-phenyl)-9H-purin-6-yl]-pyrrolidine-2-carboxylic acid dimethylamide | 434 | 1.71 |
| 7-39 | 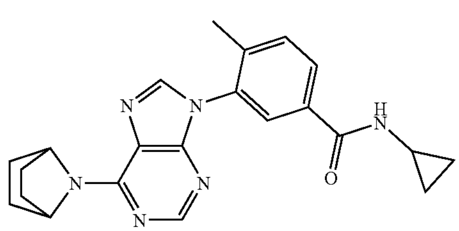 | 3-[6-(7-Aza-bicyclo[2.2.1]hept-7-yl)-purin-9-yl]-N-cyclopropyl-4-methyl-benzamide | 389 | 1.95 |

TABLE 5-continued

| Example | Name | MS [M+H]+ | HPLC C t_R (min) |
|---|---|---|---|
| 7-40 | N-Cyclopropyl-3-[6-(2,5-dimethyl-pyrrolidin-1-yl)-purin-9-yl]-4-methyl-benzamide | 391 | 1.93 |
| 7-41 | 3-(6-Benzylamino-purin-9-yl)-N-cyclopropyl-4-methyl-benzamide | 399 | 1.96 |
| 7-42 | N-Cyclopropyl-4-methyl-3-(6-piperidin-1-yl-purin-9-yl)-benzamide | 377 | 2.07 |
| 7-43 | N-Cyclopropyl-4-methyl-3-(6-morpholin-4-yl-purin-9-yl)-benzamide | 379 | 1.83 |
| 7-44 | N-Cyclopropyl-3-[6-(4-ethyl-piperazin-1-yl)-purin-9-yl]-4-methyl-benzamide | 406 | 1.44 |
| 7-45 | N-Cyclopropyl-4-methyl-3-[6-(2-methyl-piperidin-1-yl)-purin-9-yl]-benzamide | 391 | 2.22 |

TABLE 5-continued

| Example | Structure | Name | MS [M+H]+ | HPLC C $t_R$ (min) |
|---|---|---|---|---|
| 7-46 | 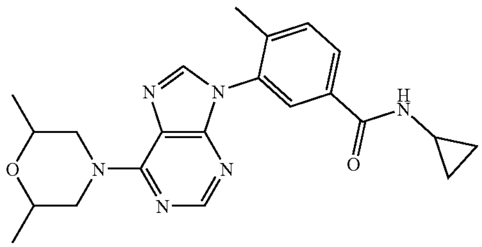 | N-Cyclopropyl-3-[6-(2,6-dimethyl-morpholin-4-yl)-purin-9-yl]-4-methyl-benzamide | 407 | 1.48 |
| 7-47 | 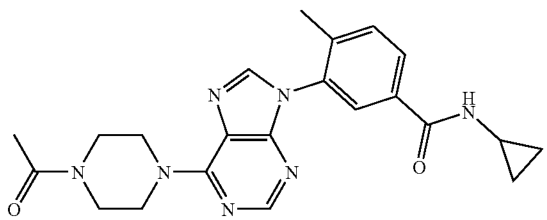 | 3-[6-(4-Acetyl-piperazin-1-yl)-purin-9-yl]-N-cyclopropyl-4-methyl-benzamide | 420 | 1.48 |
| 7-48 | 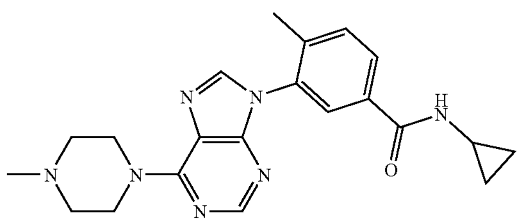 | N-Cyclopropyl-4-methyl-3-[6-(4-methyl-piperazin-1-yl)-purin-9-yl]-benzamide | 392 | 1.37 |
| 7-49 | 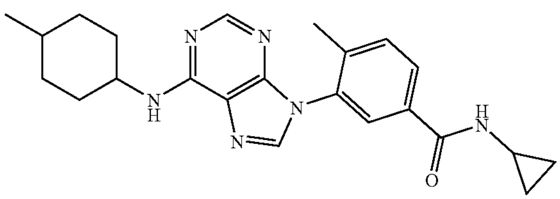 | N-Cyclopropyl-4-methyl-3-[6-(4-methyl-cyclohexylamino)-purin-9-yl]-benzamide | 405 | 2.06 |
| 7-50 | 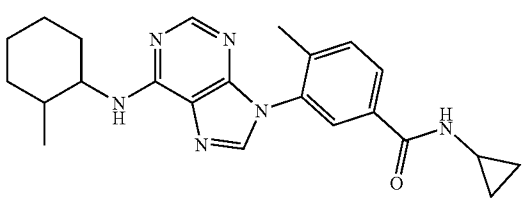 | N-Cyclopropyl-4-methyl-3-[6-(2-methyl-cyclohexylamino)-purin-9-yl]-benzamide | 405 | 2.11 |
| 7-51 | 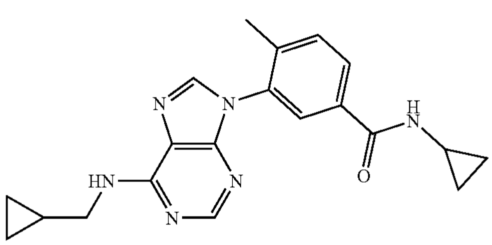 | N-Cyclopropyl-3-[6-(cyclopropylmethyl-amino)-purin-9-yl]-4-methyl-benzamide | 363 | 1.50 |

TABLE 5-continued

| Example | Structure | Name | MS [M+H]+ | HPLC C t_R (min) |
|---|---|---|---|---|
| 7-52 | 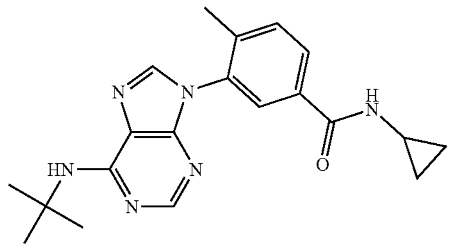 | 3-(6-tert-Butylamino-purin-9-yl)-N-cyclopropyl-4-methyl-benzamide | 365 | 2.18 |
| 7-53 | 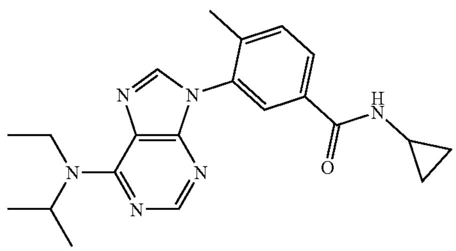 | N-Cyclopropyl-3-[6-(ethyl-isopropyl-methyl-benzamide | 379 | 2.05 |
| 7-54 | 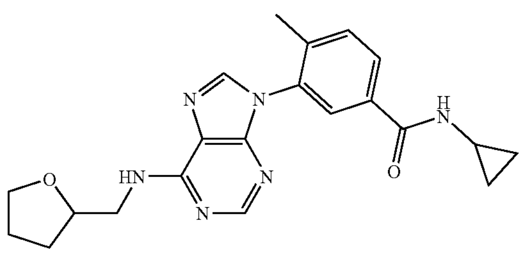 | N-Cyclopropyl-4-methyl-3-{6-[(tetrahydro-furan-2-ylmethyl)-amino]-purin-9-yl}-benzamide | 393 | 1.66 |
| 7-55 | 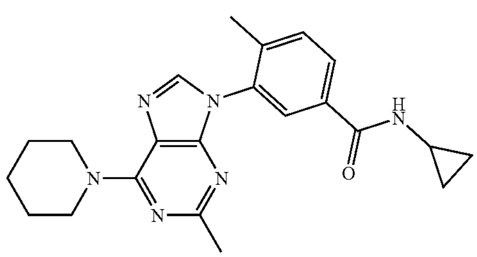 | N-Cyclopropyl-4-methyl-3-(2-methyl-6-piperidin-1-yl-purin-9-yl)-benzamide | 391 | 1.75 |
| 7-56 | 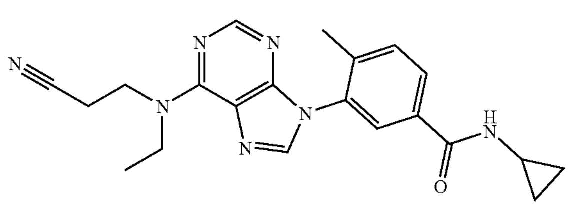 | 3-{6-[(2-Cyano-ethyl)-ethyl-amino]-purin-9-yl}-N-cyclopropyl-4-methyl benzamide | 390 | 2.10 |

TABLE 5-continued

| Example | Structure | Name | MS [M+H]+ | HPLC C $t_R$ (min) |
|---|---|---|---|---|
| 7-57 | 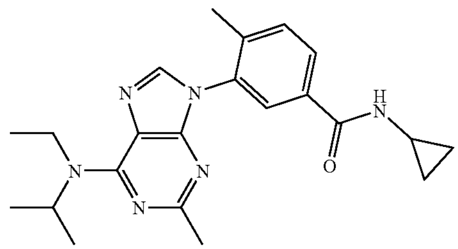 | N-Cyclopropyl-3-[6-(ethyl-isopropyl-amino)-2-methyl-purin-9-yl]-4-methyl-benzamide | 393 | 2.07 |
| 7-58 | 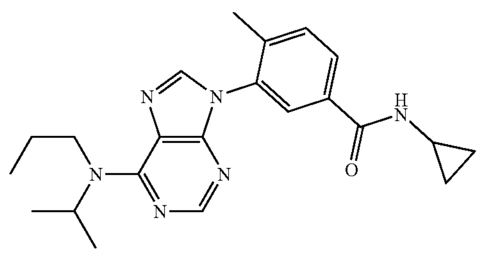 | N-Cyclopropyl-3-[6-(isopropyl-propyl-amino)-purin-9-yl]-4-methyl-benzamide | 393 | 2.35 |
| 7-59 | 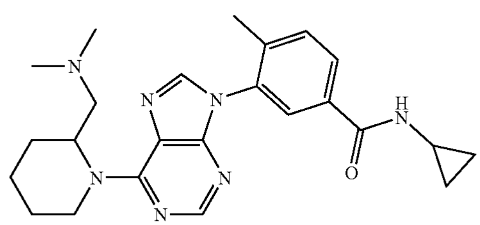 | N-Cyclopropyl-3-[6-(2-dimethylaminomethyl-piperidin-1-yl)-purin-9-yl]-4-methyl-benzamide | 434 | 1.66 |
| 7-60 | 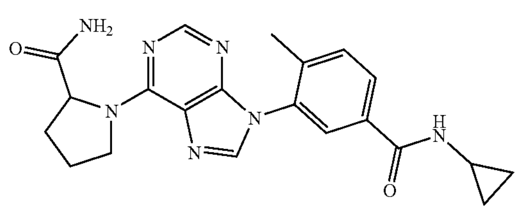 | 1-[9-(5-Cyclopropylcarbamoyl-2-methyl-phenyl)-9H-purin-6-yl]-pyrrolidine-2-carboxylic acid amide | 406 | 1.53 |
| 7-61 | 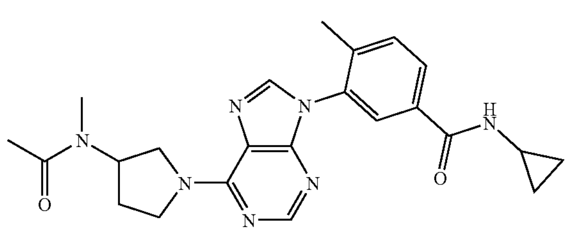 | 3-{6-[3-(Acetyl-methyl-amino)-pyrrolidin-1-yl]-purin-9-yl}-N-cyclopropyl-4-methyl-benzamide | 434 | 1.58 |

EXAMPLE 8

Preparation of N-Cyclopropyl-4-methyl-3-(6-phenyl-purin-9-ylmethyl)-benzamide

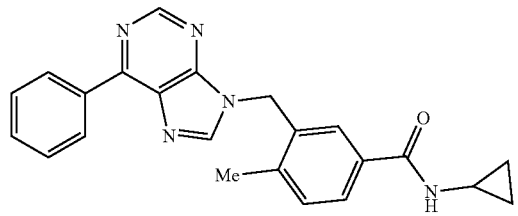

A. 3-[(5-Amino-6-chloro-pyrimidin-4-ylamino)-methyl]-N-cyclopropyl-4-methyl-benzamide To a mixture of benzylamine (41 mg, 0.2 mmol) and 4,6-dichloro-pyrimidin-5-ylamine (99 mg, 0.6 mmol) in 0.5 mL of 1-butanol was added triethyl amine (28 □1, 0.2 mmol). The reaction mixture was stirred at 80° C. for 6 hours. It was then cooled to RT. The solvent was removed under reduced pressure. The crude product was purified by a flash chromatography, eluting with 3:1 EtOAc/hexanes to give the chloride as an off-white solid (32 mg, 48%). HPLC $t_R$=1.97 min; MS m/z 332 [M+H]$^+$.

B. N-Cyclopropyl-4-methyl-3-(6-phenyl-purin-9-ylmethyl)-benzamide

The title compound was prepared using the method described in Example 4C. HPLC $t_R$=1.86 min; MS m/z 342 [M+H]$^+$.

EXAMPLE 9

Preparation of 3-(6-Cyclopentyl-purin-9-yl)-N-cyclopropyl-4-methyl-benzamide

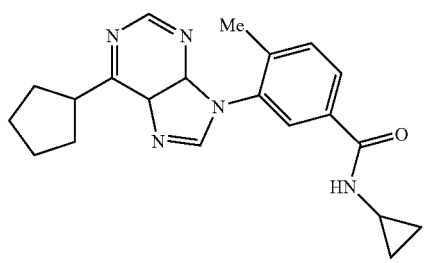

To a stirred solution of 3-(5-amino-4-cyano-imidazol-1-yl)-N-cyclopropyl-4-methyl-benzamide (140 mg) in THF (25 mL, dry) under nitrogen at room temperature was added cyclopentylmagnesium bromide (2.5 mL, 2 M in diethyl ether). The mixture was stirred at room temperature for 3 hr before solvent was removed. The residue was redissolved in EtOAc, washed by water, brine, dried over Na$_2$SO$_4$, and concentrated. The residue was redissolved in MeOH (2.0 mL), HC(OMe)$_3$ (2.0 mL) and TsOH (catalytic amount) were added. The mixture was irritated at 120° C. using microwave for 20 min. The solvent was removed and the crude product was purified by column chromatography on silica gel eluted with EtOAc, followed by further purifictaction by preparatory HPLC to give the title compound as a white solid (41.2 mg, 23%). HPLC $t_R$=2.07 min; MS m/z 362.31 [M+H]$^+$.

The following compounds were prepared in analogous fashion from the appropriately substituted grignard reagent:

Example 9-2, N-Cyclopropyl-3-(6-cyclopropyl-purin-9-yl)-4-methyl-benzamide, HPLC $t_R$=1.78 min; MS m/z 334.28 [M+H]$^+$.

Example 9-3, N-Cyclopropyl-4-methyl-3-[6-(tetrahydro-pyran-4-yl)-purin-9-yl]-benzamide, HPLC $t_R$=1.78 min; MS m/z 378.23 [M+H]$^+$.

EXAMPLE 10

Preparation of N-Cyclopropyl-4-methyl-3-(6-phenoxy-purin-9-yl)-benzamide

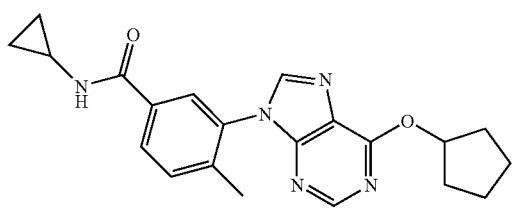

To a solution of 3-(6-Chloro-purin-9-yl)-N-cyclopropyl-4-methyl-benzamide (Example 4B) (21 mg, 0.064 mmol) in DMF (0.2 ml) was added cyclopentanol (59 □1, 0.64 mmol). The mixture was heated with microwave at 150° C. for 30 minutes. It was cooled to RT and then purified by PTLC or HPLC to give the desired as a white solid (10 mg, 0.027 mmol, 41%). HPLC $t_R$=2.09 min; MS m/z 386 [M+H]$^+$.

EXAMPLE 11

Preparation of N-Cyclopropyl-4-methyl-3-[6-(4-morpholin-4-ylmethyl-phenyl)-purin-9-yl]-benzamide

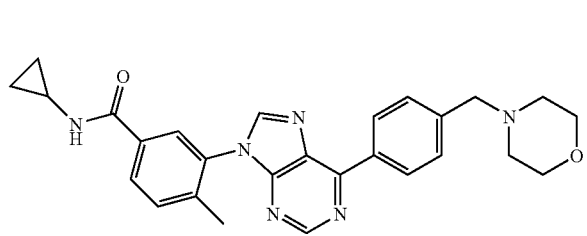

A. Preparation of 3-[6-(4-Bromomethyl-phenyl)-purin-9-yl]-N-cyclopropyl-4-methyl-benzamide To a mixture of N-cyclopropyl-3-[6-(4-hydroxymethyl-phenyl)-purin-9-yl]-4-methyl-benzamide (58 mg, 0.145 mmol, see example 4C-3 1) in dichloromethane (0.5 ml) was added carbon tetrabromide (58 mg, 0.175 mmol) then triphenylphosphine (47 mg, 0.179 mmol). The mixture was stirred at RT for an hour, then purified by a column eluting with EtOAc/Hex. (1:1) to give the desired product as a crude (88 mg, 0.19 mmol, 63%).

B. Preparation of N-Cyclopropyl-4-methyl-3-[6-(4-morpholin-4-ylmethyl-phenyl-purin-9-yl]-benzamide To a mixture of compound 11A (10 mg, 0.022 mmol) in dichloromethane (0.2 ml) was added morpholine (19 □l, 0.21 mmol). The mixture was stirred at RT for 10 minutes, and then purified by preparatory TLC with 10% MeOH/$CH_2Cl_2$ to give the desired compounds as a white solid (4.8 mg, 0.01 mmol, 47%). HPLC $t_R$=1.65 min; MS m/z 469 $[M+H]^+$.

The following compounds were prepared in analogous fashion from the appropriately substituted amine:

Example 11B-2, N-Cyclopropyl-4-methyl-3-[6-(4-morpholin-4-ylmethyl-phenyl)-purin-9-yl]-benzamide, HPLC $t_R$=1.65 min; MS m/z 469 $[M+H]^+$.

Example 11B-3, N-Cyclopropyl-3-[6-(4-dimethylaminomethyl-phenyl)-purin-9-yl]-4-methyl-benzamide, HPLC $t_R$=1.66 min; MS m/z 427 $[M+H]^+$.

EXAMPLE 12

Preparation of N-Cyclopropyl-4-methyl-3-[6-(4-methylcarbamoyl-phenyl)-purin-9-yl]-benzamide

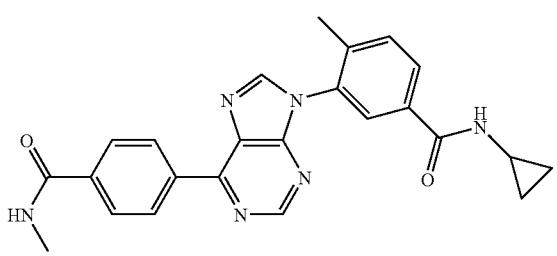

A. 4-[9-(5-Cyclopropylcarbamoyl-2-methyl-phenyl)-9H-purin-6-yl]-benzoic acid To a solution of the 4-[9-(5-Cyclopropylcarbamoyl-2-methyl-phenyl)-9H-purin-6-yl]-benzoic acid methyl ester (65 mg, 0.87 mmol) in 2 mL of tetrahydrofuran, 2 mL of methanol and 1 mL of water was added sodium hydroxide (2M, 0.15 mL, 0.3 mmol) at 20° C. The reaction mixture was stirred at that temperature for 5 hours and then the clear solution was neutralized by dropwise addition of 2N aqueous hydrochloric acid to give a solid. The product was collected by filtration to give a colorless solid (50 mg, 80%). HPLC $t_R$=2.01 min; MS m/z 414 $[M+H]^+$.

B. N-Cyclopropyl-4-methyl-3-[6-(4-methylcarbamoyl-phenyl)-purin-9-yl]-benzamide To a solution of the 4-[9-(5-Cyclopropylcarbamoyl-2-methyl-phenyl)-9H-purin-6-yl]-benzoic acid (10 mg, 0.024 mmol) and the methyl amine (3.0 mg, 0.097 mmol) in 0.5 mL of dry DMF was added 1-hydroxybenzotriazole (7.4 mg, 0.048 mmol) and 1-(3-dimethylaminopropyl)-3-ethylcarbodiimide hydrochloride (9.2 mg, 0.048 mmol) at 20° C. The reaction mixture was stirred at 20° C. for 4 hours. And then 2 mL of water was added. The product was collected by filtration to give a colorless solid (8.2 mg, 80%). HPLC $t_R$=1.99 min; MS m/z 427 $[M+H]^+$.

The following compound was prepared in analogous fashion from the appropriately substituted orthoformate:

Example 12B-2, N-Cyclopropyl-3-[6-(4-cyclopropylcarbamoyl-phenyl)-purin-9-yl]-4-methyl-benzamide, HPLC $t_R$=2.12 min; MS m/z 453 $[M+H]^+$.

EXAMPLE 13

Preparation of N-Cyclopropyl-4-methyl-3-[6-(4-[1,3,4]oxadiazol-2-yl-phenyl)-purin-9-yl]-benzamide

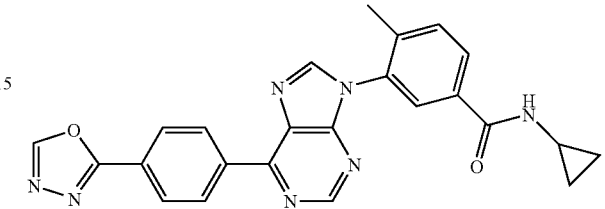

A. N-Cyclopropyl-3-[6-(4-hydrazinocarbonyl-phenyl)-purin-9-yl]-4-methyl-benzamide To a solution of the 4-[9-(5-Cyclopropylcarbamoyl-2-methyl-phenyl)-9H-purin-6-yl]-benzoic acid methyl ester (65 mg, 0.15 mmol) in 1 mL of methanol was added 1 mL of hydrazine monohydrate. The reaction mixture was stirred at room temperature for 4 hours. The methanol was removed and then 2 mL of water was added. The product was collected by filtration to give a colorless solid (47 mg, 72%). HPLC $t_R$=1.62 min; MS m/z 428 $[M+H]^+$.

B. N-Cyclopropyl-4-methyl-3-[6-(4-[1,3,4]oxadiazol-2-yl-phenyl)-purin-9-yl]-benzamide To a solution of N-Cyclopropyl-3-[6-(4-hydrazinocarbonyl-phenyl)-purin-9-yl]-4-methyl-benzamide (8.0 mg, 0.019 mmol) in 0.5 mL of trimethyl orthoformate was added three drop of acetic acid. The reaction mixture was stirred at 120° C. in microwave for 10 minutes. Then 0.5 mL of methylene chloride and 3 mL of hexanes were added. The product was collected by filtration to give a colorless solid (6.0 mg, 73%). HPLC $t_R$=2.12 min; MS m/z 438 $[M+H]^+$.

The following compounds were prepared in analogous fashion from the appropriately substituted orthoformate:

Example 13B-2, N-Cyclopropyl-4-methyl-3-{6-[4-(5-methyl-[1,3,4]oxadiazol-2-yl)-phenyl]-purin-9-yl}-benzamide, HPLC $t_R$=2.14 min; MS m/z 452 $[M+H]^+$.

Example 13B-3, N-Cyclopropyl-3-{6-[4-(5-ethyl-[1,3,4]oxadiazol-2-yl)-phenyl]-purin-9-yl}-4-methyl-benzamide, HPLC $t_R$=2.24 min; MS m/z 466 $[M+H]^+$.

The following compounds were prepared in analogous fashion from the 12A and appropriately substituted orthoformate:

Example 13B-4, N-Cyclopropyl-4-methyl-3-[6-(3-[1,3,4]oxadiazol-2-yl-phenyl)-purin-9-yl]-benzamide, HPLC $t_R$=2.12 min; MS m/z 438 $[M+H]^+$.

Example 13B-5, N-Cyclopropyl-4-methyl-3-{6-[3-(5-methyl-[1,3,4]oxadiazol-2-yl)-phenyl]-purin-9-yl}-benzamide, HPLC $t_R$=2.14 min; MS m/z 452 $[M+H]^+$.

Example 13B-6 N-Cyclopropyl-3-{6-[3-(5-ethyl-[1,3,4]oxadiazol-2-yl)-phenyl]-purin-9-yl}-4-methyl-benzamide, HPLC $t_R$=2.26 min; MS m/z 466 $[M+H]^+$.

EXAMPLE 14

Preparation of 3-(6-Cyclohexyl-2-hydroxy-purin-9-yl)-N-cyclopropyl-4-methyl-benzamide

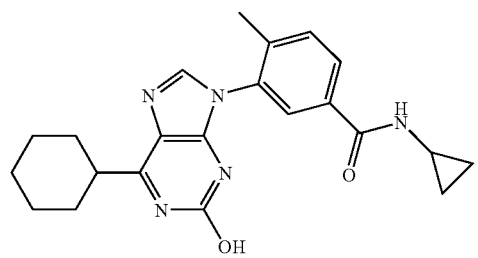

To a solution of 3-(5-amino-4-cyano-imidazol-1-yl)-N-cyclopropyl-4-methyl-benzamide (28 mg, 0.1 mmol, see Example 2A) in dry THF (5 ml) under nitrogen was added a 1 M solution of cyclohexylmagnesium bromide in THF (2M, 0.25 mL, 0.5 mmol) at room temperature. After the reaction of mixture was stirred at that temperature for 4 hours, 5 mL of water was added. The mixture was extracted with ethyl acetate (3×20 mL), washed with water and dried over $MgSO_4$, and concentrated. The crude product was dissolved in 2 mL of methylene chloride. And then 1,1-carbonyldiimidazole (32 mg, 0.2 mmol) was added. After being stirred at room temperature for 1 hour, the mixture was diluted with 50 mL of ethyl acetate and water, and the ethyl acetate layer was separated, washed with water, brine and then dried over $MgSO_4$. After filtration and concentration, the crude product was purified by preparatory HPLC to give a solid (22 mg, 57%). HPLC $t_R$=1.94 min; MS m/z 392 $[M+H]^+$.

EXAMPLE 15

The ability of the compounds provided herein to inhibit the synthesis or the activity of cytokines can be demonstrated using the following in vitro assays.

Generation of p38 Kinases cDNAs of human p38α and β were cloned by PCR. The α and β cDNAs were subcloned into DEST2 plasmid (Gateway, InVitrogen). $His_6$-p38 fusion protein was expressed in E. coli and purified from bacterial lysates by affinity chromatography using $Ni^{+2}$—NTA-agarose. $His_6$-p38 protein was activated by incubating with constitutively active MKK6. Active p38 was separated from MKK6 by affinity chromatography. Constitutively active MKK6 was generated in a manner similar to Raingeaud et al. (Mol. Cell. Biol., 1247-1255 (1996)).

TNF-α Production by LPS-Stimulated PBMCs

Heparinized human whole blood was obtained from healthy volunteers. Peripheral blood mononuclear cells (PBMCs) were purified from human whole blood by Accu-paque density gradient centrifugation and resuspended at a concentration of $5×10^6$/ml in assay medium (RPMI medium containing 10% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% $CO_2$. Following incubation, the culture medium was collected and stored at −20° C.

THP-1 cells (TIB-202, ATCC) were washed and resuspended at a concentration of $1×10^5$/ml in assay medium (RPMI medium containing 3% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% $CO_2$. Following incubation, the culture medium was collected and stored at −20° C.

TNF-α concentration in the medium was quantified using a standard ELISA kit (BioSource International, Camarillo, Calif.). Concentrations of TNF-α and $IC_{50}$ values for test compounds (concentration of compound that inhibited LPS-stimulated TNF-α production by 50%) were calculated by four parameter logistic curve (SigmaPlot, SPSS, Inc.).

p38α Assay

The p38α assay employed is based on measurement of ADP released in the reaction of interest through NADH oxidation obtained by coupling with pyruvate kinase and lactate dehydrogenase reactions. The assays were performed in 384-well UV-plates. The final volume was 25 uL prepared from the addition of 2.5 uL compound dissolved in 10% DMSO, 17.5 uL of assay buffer and 5 uL of ATP. Assay buffer contains the following reagents to give final concentration in the assay: 25 mM HEPES, 20 mM 2-glycerophosphate, pH 7.6, 10 mM $MgCl_2$, 0.1 nM sodium orthovanadate, 0.5 mM phosphoenolpyruvate, 0.12 mM NADH, 3.1 mg/ml LDH, 6.67 mg/ml pyruvate kinase, 0.25 mM peptide substrate, 2 mM DTT, 0.005% Tween 80 and 20 nM p38α kinase from Upstate. Test compounds are preincubated with p38α kinase for 60 min and the reaction started by addition of ATP to 0.15 mM final concentration. Reaction rates were measured at 340 nm using SpectraMax plate-reading spectrophotometer for 10 min at 37° C. Inhibition data were analyzed by non-linear least-squares regression using SigmaPlot.

TNF-α Production by LPS-Stimulated Mice

Mice (Balb/c female, 6-8 weeks of age, Taconic Labs; n=8/treatment group) were injected intraperitoneally with lipopolysaccharide (LPS) (50 ug/kg of E. coli strain 0111:B4, Sigma) suspended in sterile saline. Ninety minutes later, mice were sedated by $CO_2$:$O_2$ inhalation and a blood sample was obtained. Serum was separated and analyzed for TNF-α concentrations by commercial ELISA assay per the manufacturer's instructions (BioSource International). Test compounds were administered orally at various times before LPS injection. The compounds were dosed either as suspensions or as solutions in various vehicles or solubilizing agents.

Since modifications will be apparent to those of skill in the art, it is intended that the invention be limited only by the scope of the appended claims.

What is claimed is:

1. A compound of formula

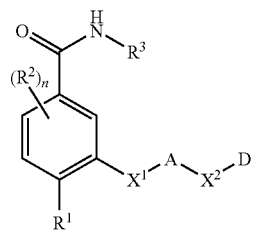

wherein $R^1$ is methyl, $R^2$ is hydrogen, n is 0, 1 or 2,

R³ is cyclopropyl,
X¹ is a single bond or alkylene,
A, X² and D are a pyrazolopyrimidine group of formula III

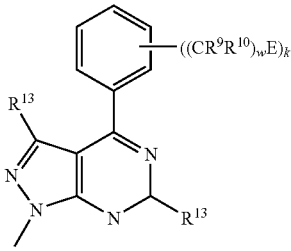

k is an integer from 0 to 4,
w is an integer from 0 to 4,
R¹³ is hydrogen, alkyl, OH or NH₂, and
(CR⁹R¹⁰)_wE is alkyl, alkoxy, halo, —CH₂-heterocyclyl, —CONH-cycloalkyl, alkylsulfonyl, alkylthio, alkylsulfonylamino, haloalkyl, aminocarbonyl, pseudohalo or heterocyclyl, or two (CR⁹R¹⁰)_wE groups, which substitute adjacent atoms on D, together form alkylenedioxy,
wherein
alkyl is lower alkyl having 1 to 6 carbon atoms,
alkylene is lower alkylene having 1 to 6 carbons,
haloalkyl is an alkyl group in which one or more of the hydrogen atoms are replaced by halogen
cycloalkyl is to a saturated mono- or multicyclic ring system of 3 to 10 carbon atoms,
alkoxy is RO—,
alkylthio is RS—,
R is lower alkyl having 1 to 6 carbon atoms
pseudohalo is cyanide, cyanate, thiocyanate, selenocyanate, trifluoromethoxy, or azido and
heterocyclyl is a monocyclic or multicyctic non-aromatic ring system of 3 to 10 members where 1 to 3, of the atoms in the ring system is a heteroatom selected from nitrogen, oxygen or sulfur or a pharmaceutically acceptable salt thereof.

2. The compound according to claim 1, wherein X¹ is a single bond.

3. The compound according to claim 1, which is selected from the group consisting of:
N-Cyclopropyl-4-methyl-3-(4-phenyl-pyrazolo[3,4-d]pyrimidin-1-yl)-benzamide,
N-Cyclopropyl-3-[4-(2-methoxy-phenyl)-pyrazolo[3,4-d]pyrimidin-1-yl]-4-methyl-benzamide,
N-Cyclopropyl-3-[4-(4-methanesulfonyl-phenyl)-pyrazolo[3,4-d]pyrimidin-1-yl]-4-methyl-benzamide,
N-Cyclopropyl-3-[4-(3.4-dimethoxy-phenyl)-pyrazolo[3,4-d]pyrimidin-1-yl]-4-methyl-benzamide, N-Cyclopropyl-3-[4-(4--methoxy-phenyl)-pyrazolo[3,4-d]pyrimidin-1-yl]-4-methyl-benzamide, N-Cyclopropyl-4-methyl-3-{4-[3-(4-methyl-piperazin-1-ylmethyl)-phenyl]-pyrazolo[3,4-d]pyrimidin-1-yl}-benzamide,
N-Cyclopropyl-3-[4-(3-ethoxy-phenyl)-pyrazolo[3,4-d]pyrimidin-1-yl]-4-methyl-benzamide,
N-Cyclopropyl-3-[4-(3-iodo-phenyl)-pyrazolo[3,4-d]pyrimidin-1-yl]-4-methyl-benzamide,
N-Cyclopropyl-3-[4-(3-methoxy-phenyl)-pyrazolo[3,4-d]pyrimidin-1-yl]-4-methyl-benzamide,
N-Cyclopropyl-3-(6-hydroxy-4-phenyl-pyrazolo[3,4-d]pyrimidin-1-yl)4-methyl-benzamide, and
N-Cyclopropyl-4-methyl-3-{4-[3-(4H-[1,2,4]triazol-3-yl)-phenyl]-pyrazolo[3,4-d]pyrimidin-1-yl}-benzamide.

4. The compound according to claim 1 in the form of a pharmaceutically acceptable salt.

5. A pharmaceutical composition comprising a compound of claim 1 and a pharmaceutically acceptable carrier.

* * * * *